United States Patent [19]

DeVore et al.

[11] Patent Number: 4,713,446

[45] Date of Patent: Dec. 15, 1987

[54] VISCOELASTIC COLLAGEN SOLUTION FOR OPHTHALMIC USE AND METHOD OF PREPARATION

[75] Inventors: Dale P. DeVore, Chelmsford, Mass.; Robert A. Scherrer, White Bear Lake; Matthew T. Scholz, Woodbury, both of Minn.

[73] Assignee: Minnesota Mining and Manufacturing Company, St. Paul, Minn.

[21] Appl. No.: 890,847

[22] Filed: Aug. 6, 1986

Related U.S. Application Data

[63] Continuation-in-part of Ser. No. 773,310, Sep. 6, 1985, abandoned.

[51] Int. Cl.$^4$ ................. A61K 31/78; A61B 17/00
[52] U.S. Cl. ..................... 530/356; 128/DIG. 8; 514/2; 514/801; 514/912; 523/113; 604/51
[58] Field of Search ............... 530/356, 353, 402; 128/DIG. 8; 604/51; 514/21, 801, 912; 523/113; 3/1

[56] References Cited

U.S. PATENT DOCUMENTS

| | | | |
|---|---|---|---|
| 2,127,841 | 8/1939 | Gellendien | 530/353 |
| 3,949,073 | 4/1976 | Daniels et al. | 424/177 |
| 4,141,973 | 2/1979 | Balazs | 424/110 |
| 4,164,559 | 8/1979 | Miyata et al. | 424/14 |
| 4,260,228 | 4/1981 | Miyata | 351/160 |
| 4,264,155 | 4/1981 | Miyata | 351/160 |
| 4,264,493 | 4/1981 | Battista | 530/356 |
| 4,268,131 | 5/1981 | Miyata et al. | 351/160 |
| 4,328,803 | 5/1982 | Pape | 128/276 |
| 4,382,081 | 5/1983 | Sundeen et al. | 424/177 |
| 4,404,033 | 9/1983 | Steffan | 106/161 |
| 4,409,332 | 10/1983 | Jefferies et al. | 435/188 |
| 4,424,208 | 1/1984 | Wallace et al. | 424/177 |
| 4,532,267 | 7/1985 | Allan | 523/106 |
| 4,540,568 | 9/1985 | Trager et al. | 424/81 |
| 4,559,304 | 12/1985 | Kasai et al. | 435/240 |

FOREIGN PATENT DOCUMENTS 0183136 6/1986 European Pat. Off. .
57-48021 3/1982 Japan .
8504413 10/1985 PCT Int'l Appl. .

OTHER PUBLICATIONS

Milos Chvapil et al., "Medical and Surgical Applications of Collagen", International Review of Connective Tissue Research, 6 (1973), 1–16.
Kurt H. Stenzel et al., "Collagen Gels: Design for a Vitreous Replacement", Science, 164 (Jun. 13, 1969), 1282–1283.
Michael W. Dunn et al., "Collagen-Derived Membrane: Corneal Implantation", Science, 157 (1967), 1329–1330.
Endre A. Balazs and Erwin Hultsch, "Replacement of the Vitreous with Hyaluronic Acid, Collagen and Other Polymers", in Advance in Vitreous Surgery, ed. by Irvine and O'Malley, (Springfield, Ill.: Charles C. Thomas, 1976), pp. 601–623.
Eiichiro Kawakami, "Operation for Aftercataract with the Injection of Collagen Gel into the Anterior Chamber, " Excerpta Medica International Congress Series, (Netherlands), 2/450, (1975), 1432–1434.
Albert L. Rubin, MD et al., "Collagen as a Vehicle for Drug Delivery, Pewliminary Report", The Journal of Clinical Pharmacology, Aug.-Sep., 1973, pp. 309–312.
Albert L. Rubin et al., "Collagen: Medical and Surgical Applications", Journal of Macromolecular Science—Chemistry, A3(1), (Jan. 1969), 113–118.
P. Payrau et al., "Experimental Applications of Collagen in Ophthalmology", Archives of Ophthalmology, 23(2), (1963), 9.
Kevin Weadock et al., "Evaluation of Collagen Cross-linking Techniques", Biomaterials, Medical Devices, and Artificial Organs, 11(4), (1983–1984), 293–318.
Roger L. Simpson, "Collagen as a Biomaterial", pp. 109–117.
Ronald C. Pruett, MD et al., "Collagen Vitreous Substitute", Arch Ophthal, 88 (Nov. 1982), 540–543.
Georg Eisner, "General Considerations Concerning Viscous Materials in Ophthalmic Surgery", Transactions of the Ophthalmological Society in the United Kingdom, 103 (1983), 247–253.
G. J. Hart et al., "The Effects of Certain Glycols, Substituted Glycols and Related Organic Solvents on the Thermal Stability of Soluble Collagen", The Biochemical Journal, 125 (1971), 599–604.
Allan E. Russell, "Effect of Alcohols and Neutral Salt on the Thermal Stability of Soluble and Precipitated Acid-Soluble Collagen", Journal of Biological Chemistry, 131 (1973), 335–342.
Erwin Hultsch, MD, PhD; "The Scope of Hyaluronic Acid as an Experimental Intraocular Implant", Ophthalmology, 87(7), (Jul. 1980), 706–712.
Endre A. Balazs and D. Brendan Sweeney, "The Injection of Hyaluronic Acid and Reconstituted Vitreous into the Vitreous Cavity", in New and Controversial Aspects of Retinal Detachment, ed. by A. McPherson, (New York: Hoeber Medical Division, Harper & Row, 1968), pp. 371–376.

*Primary Examiner*—Howard E. Schain
*Assistant Examiner*—Nathan M. Nutter
*Attorney, Agent, or Firm*—Donald M. Sell; James A. Smith; Jennie G. Boeder

[57] ABSTRACT

Chemically-modified collagen is prepared by reacting native collagen with a di or tri-carboxylic acid halide, di or tri-sulfonyl halide, di or tri-anhydride, or di or tri-reactive active ester coupling agent. The reaction is done in a controlled manner so that the degree of cross-linking is limited. Any remaining lysine epsilon amino groups present in the coupled collagen product may be converted to carboxyamido or sulfonamido groups by acid halide, anhydride, sulfonyl halide or active ester amine-modifying agents. The resultant product when dissolved in a physiological buffer provides a viscoelastic solution having therapeutic application in a variety of surgical procedures, particularly in ophthalmic surgery. This viscoelastic solution "melts," i.e., exhibits a dramatic loss of viscosity, when subjected to temperatures of between 32° and 48° C.

31 Claims, No Drawings

VISCOELASTIC COLLAGEN SOLUTION FOR OPHTHALMIC USE AND METHOD OF PREPARATION

This is a continuation-in-part of application Ser. No. 773,310 filed Sept. 6, 1985 and now abandoned.

FIELD OF THE INVENTION

This invention relates to a chemically-modified collagen compound which when dissolved in a physiological buffer has therapeutic application in a variety of medical applications, particularly in ophthalmic surgery. Specifically, the collagen solutions of this invention are useful in the following procedures: (a) as an anterior segment implant to maintain anterior chamber depth and to protect the corneal endothelium during intracapsular and extracapsular cataract lens extraction and during intraocular lens implantation; (b) as a surgical adjunct during corneal transplant surgery to protect the corneal endothelium from contacting other ocular tissue and to prevent post-operative graft dislocation; (c) as a posterior segment implant during intraocular lens implantation and as an adjunct to retinal detachment surgery; and (d) as a vitreous replacement. This invention also relates to the production of the collagen compound by reacting purified, native, pepsin-treated collagen with an amine-reactive coupling agent and a monofunctional amine-reactive modifying agent, either sequentially or simultaneously, and in a controlled manner so as to limit the degree of coupling.

BACKGROUND OF THE INVENTION

Sodium hyaluronate, collagen gels and chondroitin sulfate solutions have been used in the anterior chamber to protect the corneal endothelium from intraocular lens trauma and to maintain anterior chamber depth. Additionally, hyaluronate and collagen gels have been used as vitreous replacements. None of these materials has proven to be ideal in such applications.

Chondroitin sulfate solutions do not exhibit pseudoplastic behavior, i.e., the viscosity is relatively constant at all shear rates. Accordingly, chondroitin sulfate solutions do not exhibit the same degree of anterior chamber support as pseudoplastic fluids such as those prepared using sodium hyaluronate. Furthermore, since the viscosity of the chondroitin sulfate solutions does not decrease at increasing shear rates (as do pseudoplastic materials) extremely high pressures are needed to apply or irrigate chondroitin sulfate solutions through a syringe (MacRae et al., "The Effects of Sodium Hyaluronate, Chondroitin Sulfate, and Methyl Cellulose on the Corneal Endothelium and Intraocular Pressure," *American Journal of Ophthalmology*, 95:332–341 (1983)). Additionally, commercially available chondroitin sulfate solutions (20 to 50 percent solutions) have osmolarities in excess of 500 mOs$_m$. Such high osmolarities are detrimental to the corneal endothelium. Lastly, as reported by MacRae et al. in the American Journal of Ophthalmology, supra, 20 percent chondroitin sulfate may cause a sharp increase in intraocular pressure in the first one to four hours after intracameral injection and, therefore, anterior chamber washout is indicated.

Stenzel et al. ("Collagen Gels: Design for a vitreous Replacement", *Science* 164: 1282–1283 (1969)), Dunn et al. ("Collagen-Derived Membrane: Corneal Implantation", *Science*, 157: 1329–1330 (1967)) and Rubin et al. ("Collagen as a Vehicle for Drug Delivery", *J. Clinical Pharmacology*, Aug–Sept., Pages 309–312 (1973)) have described the use of stabilized collagen membranes and gels to serve as drug delivery devices, vitreous replacement gels and cornea transplants. Introduction of crosslinks was accomplished by heat, ultraviolet radiation or glutaraldehyde reaction.

U.S. Pat. No. 4,409,332 discloses membranes and gels composed of complexes of reconstituted collagen with alkaline phosphatase, crosslinked with glutaraldehyde, UV radiation or gamma radiation. These complexes are said to be useful as vitreous replacements for ophthalmologic therapy.

U.S. Pat. No. 4,164,559 describes a chemically-modified collagen membrane which is useful as a carrier for ophthalmic medication. The collagen compounds disclosed are single collagen units which have been acylated or esterified.

Collagen as an anterior chamber replacement is described by Kawakami ("Operation for Aftercataract with the Injection of Collagen Gel into the Anterior Chamber", *Excerpta Medica International Congress Series*, Vol. 2 (450), pages 1432–1434 (1975)). This investigation describes the injection of ultraviolet crosslinked collagen gel into the anterior chamber prior to extraction of the aftercataract.

The collagen gels described hereinabove have greater viscosities and thus afford more protection and support to eye tissues than does chondroitin sulfate. However, known collagen gels are not pseudoplastic and fragment into small pieces when injected through a syringe. Additionally, collagen gels are generally hazy materials and have been known to cause inflammatory reactions in the anterior chamber and the vitreous (Advances in vitreous Surgery, pages 601–623, Irvine and O'Malley, 1976).

Furthermore, collagen gels injected into the anterior chamber may cause an elevation of intraocular pressure (Kawakami, E., "Operation for Aftercataract with the Injection of Collagen Gel into the Anterior Chamber", supra).

Neither the chondroitin sulfate solutions nor the collagen gels used in ophthalmic surgery are viscoelastic materials. Viscoelastic ophthalmic materials are preferred for several reasons. During surgery, viscoelastic materials protect cell and tissue surfaces from mechanical trauma; create space by separating two adjacent but not adherent tissue surfaces, or by breaking normal or pathological tissue adhesions; maintain space allowing for safe surgical manipulations or by permitting the insertion of implants without dislocating or touching sensitive tissues; contain hemorrhages; and also act as a "soft instrument" or "surgical tool" to move, manipulate or relocate tissues.

After surgery, viscosurgical materials may be used to retain space for a desired period of time, prevent or minimize postsurgical inflammation and localize bleeding, restrain fibrin coagulation, hold back inflammatory cells, and lubricate tissue surfaces which move relative to each other and thereby prevent adhesion formation.

U.S. Pat. No. 4,141,973 discloses the use of highly-pure hyaluronic acid for both vitreous and aqueous replacement. This material is colorless, transparent, nontoxic and viscoelastic. However, it too has a number of drawbacks. The most abundant natural source of hyaluronic acid is rooster combs. Due to the low yield from this source coupled with the relatively complicated process involved in extracting and isolating this compound, hyaluronic acid is an expensive product.

Secondly, while hyaluronic acid appears to be efficacious in reducing endothelial cell damage and in maintaining the anterior chamber during surgical manipulation, reports of elevated intraocular pressure, postoperatively, have been documented and it is recommended that this substance be removed from the anterior chamber prior to closing the corneal incision (MacRae et al., "The Effects of Sodium Hyaluronate, Chondroitin Sulfate and Methyl Cellulose on the Corneal Endothelium and Intraocular Pressure," supra). Lastly, hyaluronic acid does not adhere to intraocular lens surfaces or surgical instruments. By way of contrast, if one dips an intraocular lens into the viscoelastic collagen solution of this invention, the solution adheres to the surface of the intraocular lens, thereby providing an increased degree of endothelial protection.

SUMMARY OF THE INVENTION

The present invention provides a chemically-modified collagen compound which comprises two or more native collagen molecules which are coupled at at least one lysine epsilon amino group present on each collagen molecule by a dicarbonyl, tricarbonyl, disulfonyl, or trisulfonyl coupling group, or a coupling group comprising a plurality of moieties, at least two or three of which are selected from the group consisting of carbonyl or sulfonyl groups. The carbonyl and/or sulfonyl groups present in the coupling group are linked to each other through saturated or unsaturated alkylene, arylene or mixed alkylene-arylene coupling chains having less than about twenty carbon atoms. The alkylene and/or arylene coupling chains may contain heteroatoms, e.g., O, S or N, and may be substituted in available aromatic positions by carboxyl groups, straight or branched chain alkyl groups of about 1 to 4 carbon atoms, straight or branched chain alkoxy groups of about 1 to 4 carbon atoms, halogens and other non-reactive moieties, and in available aliphatic positions by carboxyl groups and alkyl or alkoxy groups of about 1 to 4 carbon atoms.

More specifically, the coupling group has the general formula

—B—A—B— wherein
B is independently CO, SO$_2$ or combinations thereof;
A is selected from any one of the following:
(1) an aromatic group having about 6 to 20 carbon atoms;

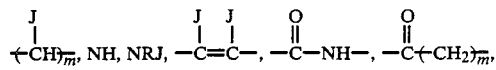

wherein
Ar is independently an aromatic ring having 6 to 10 carbon atoms or a heteroaromatic ring containing atoms selected from the group consisting of C, N, O and S, and having about 5 to 10 atoms, or combinations thereof;
J is hydrogen or $-(L)_b$B wherein L is selected from the group consisting of phenylene, an alkylene of about 1 to 4 carbon atoms and an oxyalkylene of about 1 to 4 carbon atoms, b is 0 or 1, and B is as described hereinabove, with the proviso that only one J in the chain may be $-(L)_b$B, in which case all other J's are hydrogen; n is 0 or 1;
a is an integer between about 0 and 4; and D is independently O, CO, S, SO, SO$_2$,

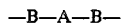, NH, NRJ, —C=C—, —C—NH—, —C+CH$_2$+$_m$,

—SO$_2$—NH—, —NH—CO—NH—, wherein m is about 1 to 3, R is selected from the group consisting of phenyl, and a straight or branched chain alkyl or acyl group having about 1 to 4 carbon atoms; and J is as defined and restricted hereinabove;
(3) an aromatic group having about 6 to 10 carbon atoms, wherein said aromatic group may be substituted in available positions by J wherein J is as defined and restricted hereinabove;
(4) a heteroaromatic group containing atoms selected from the group consisting of C, N, O and S, and having from about 5 to 14 ring atoms, wherein said heteroaromatic group may be substituted in available positions by J, wherein J is as defined and restricted hereinabove;
(5) an aliphatic or arylaliphatic chain which contains one or two olefinic or acetylenic groups and which contains about 2 to 20 carbon atoms, wherein said chain may be substituted in available positions by J, wherein J is as defined and restricted hereinabove;
(6) an alicyclic ring which may be partially unsaturated, having about 3 to 15 carbon atoms, wherein said alicyclic ring may be substituted in available positions by J wherein J is as defined and restricted hereinabove;
(7) a heterocyclic ring which may be saturated or unsaturated and which contains atoms selected from the group consisting of C, N, O and S, and which has from about 5 to 12 ring atoms, wherein said heterocyclic ring may be substituted in available positions by J wherein J is as defined and restricted hereinabove;

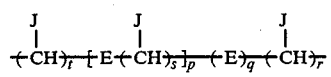

wherein
t is about 1 to 8;
E is independently O, NRJ, S, SO, SO$_2$, CO,

CONH, SO$_2$NH or NHCONH, wherein
R is as defined hereinabove, m is about 1 to 3;
J is as defined and restricted hereinabove;
s is about 2 to 8;
p is about 0 to 4;
q is about 0 or 1; and
r is about 0 to 8, provided that when
q is 1, r is greater than 0; and

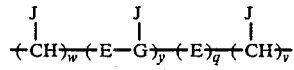

wherein
G is independently an aromatic ring having about 6 to 10 carbon atoms, or a heteroaromatic ring having about 5 to 10 atoms, or a heterocyclic ring having about 5 to 10 atoms, wherein the heteroaromatic and heterocyclic rings contain atoms selected from the group consisting of C, N, O and S;

J is as defined and restricted hereinabove; w is about 1 to 8;

E and q are as defined hereinabove;

Y is about 1 or 2; and v is between about 0 and 4, provided that when q is 1, v is not 0.

Aromatic or heteroaromatic portions of A may be substituted in available positions by carboxyl groups, straight or branched chain alkyl groups of about 1 to 4 carbon atoms, straight or branched chain alkoxy groups of about 1 to 4 carbon atoms, halogens and other non-reactive moieties. Aliphatic, alicyclic and heterocyclic portions of A may be substituted in available positions by carboxyl groups and straight or branched chain alkyl groups of about 1 to 4 carbon atoms.

The present invention also provides a chemically-modified collagen compound which comprises two or more native collagen molecules coupled as described above, wherein at least a portion of the remaining basic nitrogens present on the coupled collagen (principally amine groups) are converted to carboxyamido or sulfonamido groups, which groups preferably contain at least one carboxyl or sulfonic acid moiety, by acid halide, anhydride, sulfonyl halide or active ester amine-modifying agents. That is, at least a portion of the uncoupled lysine epsilon amino groups present on the coupled collagen product are linked to amine-modifying groups, which amine-modifying groups are saturated or unsaturated alkane, arene or mixed alkane-arene sulfonamide or carboxamide groups having between about 2 and 20 carbon atoms, which are terminated by one or two carboxylic or sulfonic acid moieties. The amine-modifying groups may also contain up to about five heteroatoms, e.g., O, S and N, and may be substituted in available aromatic and aliphatic positions by carboxyl groups, alkyl or alkoxy groups of about 1 to 4 carbon atoms, halogens and other non-reactive moieties. More specifically, the amine-modifying groups have the general formula:

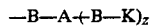

wherein z is 0 to 2, preferably, 1 or 2, B and A are as defined hereinabove with the proviso that J is hydrogen, and K is OH.

The chemically-modified collagen compound of the present invention is prepared by coupling purified, pepsin-treated collagen to a limited extent, accompanied by the modification of uncoupled basic nitrogens (principally amine groups) by a modifying agent which renders these sites nonbasic, i.e., having a pKa of less than 4.

Applicants have found that the degree of coupling is highly important in producing collagen solutions having viscoelastic, pseudoplastic properties which allow them to be used successfully as aqueous or vitreous replacements in ophthalmic surgery. It has been found that if the coupling is too extensive, the product produced is not a viscoelastic solution, but is instead a collagen gel. The difficulties with such gels are detailed hereinabove. It has also been discovered that if the coupling is not extensive enough the solution will not be as viscoelastic as desired and will not possess the lubricative properties necessary for an ophthalmic surgery aid. Applicants have also found that it is necessary to render nonbasic most of the remaining uncoupled basic sites present on the coupled collagen molecules, preferably at the same time introducing a negatively charged group, in order for the collagen product to resist fibrillogenesis.

The collagen solutions prepared according to the method of the present invention are found to be particularly useful in ophthalmic surgery since:

(1) they are viscoelastic and possess lubricative properties which provide a degree of protection for the corneal endothelium, iris and retina;

(2) they are pseudoplastic and thus are easily injected through a syringe, yet have the ability to regain their original static viscosity;

(3) they are resistant to spontaneous fibrillogenesis, and thus retain their clear transparent nature, after insertion in the eye;

(4) they adhere to hydrophobic polymeric surfaces such as polymethylmethacrylate or polypropylene intraocular lenses, and thus can be used to coat such lenses to facilitate insertion into the anterior or posterior chamber of the eye;

(5) when injected into tissues, they decrease in viscosity and dilute into the tissue fluid, leaving the site;

(6) they will not adversely increase intraocular pressure;

(7) they have low osmolarities of between about 200 to 400 mOs; and (8) preferred embodiments are noninflammatory and biologically compatible.

Additionally, native collagen is available from a wide variety of sources, e.g. bone, tendon, hide, etc. Accordingly, collagen is more abundant and less expensive to obtain than tissue derived hyaluronic acid.

DETAILED DESCRIPTION OF THE INVENTION

The process by which the chemically-modified collagen compound is prepared comprises four major steps. These steps are (not necessarily in this order):

I. Collection of Collagen Source Material;

II. Controlled Coupling of Collagen Source Material;

III. Modification of Remaining Uncoupled Basic Sites; and

IV. Collection, Purification and Reconstitution of Modified Collagen.

I. Collection of Collagen Source Material

The method of obtaining the collagen from the crude collagen source, e.g. tendon, hide, etc., is normally not critical, and some flexibility may be used in the selection of the particular tissue and the method applied thereto. Applicants prefer to extract collagen from a connective tissue, such as bovine hide. If the collagen is to be used for ophthalmic applications, it is preferred that it be obtained solely from the corium layer of the bovine hide, otherwise known as "split" hides. Split hides are commercially available from the Andre Manufacturing Co., Newark, New Jersey.

The collagen may be solubilized by any of the standard extraction methods, e.g. acid or salt extraction, enzyme-digestion, or a combination of these. Preferably, dehaired and cleaned hide is solubilized with a proteolytic enzyme (pepsin, for example) and solubilized collagen is precipitated at pH 7, after inactivation and removal of the enzyme, by addition of NaCl to about 2.5M. Pepsin-treated collagen precipitates leaving behind in solution (to be discarded) the digested nonhelical terminal peptides of the collagen molecule and other non-collagenous contaminates, e.g. saccharides, mucopolysaccharides, etc. Inactivated enzymes are removed by filtration and centrifugation at 4° C. The pepsin-treated collagen is then further purified by repeating redissolution in acidic water (pH 2–4) and reprecipitation by salt treatment, e.g. by the addition of 0.8M sodium chloride solution at pH 3.

The purified collagen is preferably diafiltered using, for example, an Amicon DC-30 filtration system, commercially available from Amicon, Danvers, Mass. Preferably, a 0.1μ membrane filter is employed to filter out salts, proteins and other molecules having a molecular weight of less than 300,000 daltons. Applicants have found that diafiltration increases the transparency of the collagen product and may aid in reducing the incidence of aqueous flare. Additionally, if the collagen is to be used in surgical applications, it must be sterilized, preferably by filter sterilization techniques.

II. Controlled Coupling

The solubilized purified collagen molecules are coupled using coupling agents which have two or three groups which react with amines but do not react with carboxyl groups. Such coupling agents include di- and tri-carboxylic acid halides, di- and tri-sulfonyl halides, di- and tri-anhydrides, di- and tri-reactive active esters and coupling agents containing at least two groups of the carboxylic acid halide, sulfonyl halide, anhydride or active ester type. Preferred aromatic and aliphatic di- and tri-carboxylic acid halides include d-camphoric diacid chloride; 4-[-p-(o-chlorocarbonylbenzoyl)-phenyl]butyryl chloride; furan-3,5-dicarboxylic chloride; fumaryl chloride; glutaryl chloride; succinyl chloride; sebacoyl chloride; isophthaloyl chloride; terephthaloyl chloride; 4-bromoisophthaloyl chloride; diglycolic diacid chloride; 1,1-cyclohexanediacetyl chloride; 2,2-dimethylglutaryl chloride; thioglycolic acid dichloride; nitrilotriacetyl chloride; beta-methylcarballylic acid trichloride; hexadecanedioic acid dichloride; malonic acid dichloride; acetone dicarboxylic acid dichloride; oxydiacetyl chloride benzene-1,3,5-tricarbonyl chloride; 4-chlorocarbonylphenoxyacetyl chloride; homophthaloyl chloride; 4,4'-diphenyletherdicarboxylic acid dichloride; 4,4'-diphenylthioetherdicarboxylic acid dichloride; 4,4'-diphenylsulfonedicarboxylic acid dichloride; acetylene dicarboxylic acid dichloride; cyclohexane-1,4-dicarboxylic acid dichloride; trans-3,6-endomethylene-1,2,3,6-tetrahydrophthaloyl chloride; 4,4'-dithiodibutyryl chloride; diphenylmethane-4,4'-bis-(oxyacetyl) chloride; N-(4-chlorocarbonylphenyl)anthranyloyl chloride; 1,3-benzenebisoxyacetyl chloride; pyridine-3,5-dicarboxylic acid dichloride; pyridine-2,5-dicarboxylic acid dichloride; pyridine-2,4-dicarboxylic acid dichloride; pyrazine-2,3-dicarboxylic acid dichloride; and pyridine-2,6-dicarboxylic acid dichloride; ethyleneglycol bis-(-4-chlorocarbonylphenyl)ether; diethyleneglycol bis-(-4-chlorocarbonylphenyl)ether; bis-(-4-chlorocarbonyl-2-tolyl)thioether; and N-chlorocarbonylmethyl-N-methylglutaramic acid chloride.

Preferred aromatic and aliphatic di- or trisulfonyl halides include para-fluorosulfonylbenzenesulfonyl chloride; 1,3,5-benzenetrisulfonyl chloride; 2,6-naphthalenedisulfonyl chloride; 4,4'-biphenyl disulfonyl chloride; 1,10-decane-disulfonyl chloride; and 4,4'-trans-stilbenedisulfonyl chloride.

Preferred di- and trianhydride coupling agents include 1,2,4,5-benzenetetracarboxylic dianhydride; 3,4,9,10-perylene tetracarboxylic dianhydride; 3,3',4,4'-benzophenonetetracarboxylic dianhydride; 1,2,7,8-naphthalenetetracarboxylic dianhydride; pyromellitic dianhydride; 2,3,4,5-tetrahydrofurantetracarboxylic acid dianhydride; mellitic trianhydride; 1,2,3,4-cyclobutanetetracarboxylic dianhydride; bicyclo[2,2,2]oct-7-ene-2,3,5,6-tetracarboxylic dianhydride; cyclopentanetetracarboxylic dianhydride; ethylenediaminetetraacetic dianhydride; and diethylenetriaminepentaacetic dianhydride.

Active esters are described by Greenstein and Winitz in "Chemistry of the Amino Acids", vol. 2, John Wiley and Sons, Inc. (1961). Preferred direactive active ester coupling agents include diphenyl succinate; bis(p-nitrophenyl) succinate; bis(cyanoethyl) glutarate; and di-S-phenyl dithiosuccinate.

Preferred coupling agents containing combinations of amine-reactive groups include 5-chlorosulfonyl- ortho-anisic acid chloride; 2-chloro-5-fluorosulfonylbenzoyl chloride; 4-chlorosulfonylphenoxyacetyl chloride; meta-fluorosulfonylbenzoyl chloride; and trimellitic anhydride acid chloride.

The coupling agent is added to and mixed thoroughly with an aqueous solution of the pepsin-treated collagen. Preferably, in order to limit the degree of coupling, the reaction mixture contains purified collagen in a concentration of 0.05 to 0.3 percent by weight, and more preferably 0.15 to 0.3 percent by weight.

The concentration of the coupling agent is dependent upon many factors including the reactivity of the coupling agent. In general, however, the amount of the coupling agent is about 1 to 600 moles of coupling agent per mole of collagen, preferably about 50 to 500 moles of coupling agent per mole of collagen and more preferably about 100 to 200 moles of coupling agent per mole of collagen.

The pH of the reaction mixture is preferably maintained throughout the coupling reaction at about 8 to 11, preferably at about 8.5 to 9.5, and most preferably at about 9.0, by addition of a dilute base, e.g., 1N sodium hydroxide. In this manner, almost all of the lysine epsilon amino groups present on the collagen molecules are freed from their protonated form, and become capable of reaction with either the coupling agent or the modifying agent.

The coupling reaction is continued until substantially all, i.e., at least 90 percent, of the coupling agent has either reacted with the collagen or been hydrolyzed, normally about thirty minutes.

The degree and uniformity of the coupling reaction is dependent upon, and thus is controlled by the temperature, the solvent used to dissolve the coupling agent, the rate of addition of the coupling agent, the identity and form of the coupling agent, the concentration of the reactants, and the pH variations of the reaction mixture.

For example, some coupling agents are preferably added to the collagen solution as a solid. Applicants have found that by adding the coupling agent to the collagen as a solid, the degree of coupling can be controlled. However, while addition of certain coupling agents in solid form is preferred, the coupling agent may be dissolved in a suitable solvent before addition to the pepsin-treated collagen. Suitable solvents are preferably water miscible and include N-methylpyrrolidone; N,N-dimethylformamide; acetone; ethylene glycol dimethyl ether; and acetonitrile. The particularly-preferred solvents have relatively high dielectric constants, i.e., greater than 25 and preferably greater than 30 when measured at 25° C. Such particularly-preferred solvents include N-methylpyrrolidone and N,N-dimethylformamide. Solvents with high dielectric constants offer another means of controlling the coupling since they tend to limit the degree of coupling by promoting hydrolysis of the coupling agent. Alternatively, relatively water-immiscible solvents may be used, giving a two phase reaction mixture. The use of a two phase mixture limits the degree of coupling by limiting the number of reaction sites to the surface of the solvent. An example of a relatively water-immiscible solvent is ethyl acetate. When a solution of the coupling agent in any solvent is used it is preferred that the amount of solvent be such that there is present about 0.5 to 10 ml of solvent per 100 ml of aqueous collagen solution and most preferably about 1 ml of solvent per 100 ml of collagen solution.

While the coupling reaction can be conducted at a temperature of between about 0° and 35° C., Applicants have found that by allowing the coupling reaction to proceed at a temperature below about 20° C., preferably about 4° C., the reaction of the coupling agent with lysine epsilon amino groups present on the collagen can be encouraged.

The particularly-preferred couplers include succinyl chloride; glutaryl chloride; terephthaloyl chloride; bicyclo-(2,2,2)-oct-7-ene-2,3,5,6-tetracarboxylic-2,3,5,6-dianhydride; 1,2,4,5-benzenetetracarboxylic dianhydride; p-fluorosulfonylbenzenesulfonyl chloride; and 1,3,5-benzenetrisulfonyl chloride, diethylene triamine pentaacetic dianhydride.

Applicants have found that with certain highly-reactive coupling agents such as terephthaloyl chloride; bicyclo-(2,2,2)-oct-7-ene-2,3,5,6-tetra- carboxylic-2,3,5,6-dianhydride; 1,2,4,5-benzenetetracarboxylic dianhydride; and p-fluorosulfonylbenzenesulfonyl chloride; or with solvent systems of high dielectric constant and/or relatively high water miscibility, such as N,N-dimethylformamide and N-methylpyrrolidone, the coupling reaction is preferably begun by premixing the reactants at an acidic pH of about 3 to 5.5, before raising the pH to between 8 and 11 to affect reaction of the collagen amine groups with the coupling agent. By varying the pH in this manner, the coupling reaction is controlled to achieve the desired viscoelastic product.

It is preferred, particularly with coupling agents of lesser reactivity, that the pH of the reaction mixture be increased to at least 11.5 at the completion of the coupling reaction in order to hydrolyze any unreacted portions of the coupling agent.

III. Modification of Remaining Basic Sites

The coupled collagen product contains reactive basic sites, principally amine groups, which in order to produce a clear and transparent solution for ocular surgery must be chemically modified to provide a net neutral or preferably negative charge. Such modification of these reactive basic sites will enable the collagen product to resist fibril formation when used in ophthalmic surgery. To this end the coupled collagen is reacted with a mono-reactive amine-modifying agent, also known as a monoacylating or sulfonating agent. The modifying agent is preferably a compound, or combination of compounds which contains an acidic, carboxylic or sulfonic group or generates an acidic, carboxylic or sulfonic group during reaction. Preferably, the acid form of the modifying agent has a similar pKa to that of the hydrolyzed coupling agent in order to insure optimum precipitation of the chemically-modified collagen product. Useful modifying agents include anhydrides, acid halides, sulfonyl halides and active esters. Preferred anhydrides include cyclic anhydrides, such as glutaric anhydride; 3-ethyl-3-methylglutaric anhydride; alpha-2-carboxyethyl glutaric anhydride; 3-methylglutaric anhydride; 2-phenylglutaric anhydride; dimethylglutaric anhydride; 1,8-naphthalic anhydride; 4-chloro-1,8-naphthalic anhydride; 3,6-dinitro-1,8-naphthalic anhydride; 3-nitro-1,8-naphthalic anhydride; maleic anhydride; bromomaleic anhydride; dichloromaleic anhydride; succinic anhydride; S-acetyl mercaptosuccinic anhydride; 2,2,3,3-tetramethyl succinic anhydride; 2-dodecen-1-yl succinic anhydride; methyl succinic anhydride; citraconic anhydride; itaconic anhydride; 2,3-quinoxalinedicarboxylic anhydride; 1,2-cyclobutane dicarboxylic anhydride; diphenic anhydride; cyclohexane-1,2-dicarboxylic anhydride; phthalic anhydride; hexahydro-4-methyl phthalic anhydride; homophthalic anhydride; tetrahydrophthalic anhydride; tetrachlorophthalic anhydride; tetrabromophthalic anhydride; 1,4,5,6,7,7-hexachloro-5-norborene-2,3-dicarboxylic anhydride; 3,6-endoxo-1,2,3,6-tetrahydrophthalic anhydride; 5-chloroisatoic anhydride; 3,4-pyridine dicarboxylic anhydride; carbobenzyloxy-L-glutamic anhydride; 1,2,4-benzenetricarboxylic anhydride; o-sulfobenzoic anhydride; thiodiglycolic anhydride; 2,3-pyridine dicarboxylic anhydride; 3-ketoglutaric anhydride-(1,3-acetone dicarboxylic anhydride); diglycolic anhydride; 4-amino-1,8-naphthalic anhydride; and camphoric anhydride. Preferred sulfonyl chlorides include chlorosulfonylbenzenesulfonic acid. Preferred acid chlorides include sulfoacetyl chloride, the monoacid chlorides of terephthalic acid and fumaric acid, and monomethyl succinate acid chloride. Preferred active esters include phenolates, such as monophenyl terephthalate and cyanomethyl esters such as mono(cyanomethyl succinate). Additionally, acylating agents such as benzoyl chloride, benzenesulfonyl chloride and butyrylchloride which do not produce negatively charged products may be used, but preferably in combination with the above modifiers.

The modification reaction is run in an aqueous medium so that competing reactions of acylation of the collagen amines and hydrolysis of the modifying agent occur simultaneously. As in the coupling reaction, the extent of each reaction depends on the pH, the percentage of remaining basic sites on the coupled collagen, the temperature, and the nature and form of the modifying agent.

The modifying agent may be added to an aqueous solution of the coupled collagen either neat or in a solvent. Suitable solvents are those which are used to dissolve the coupling agent. Preferably the modifying agent is added as a solid or in a water-miscible solvent having a dielectric constant less than about 25. When a solution of the modifying agent in a solvent is used it is preferred that the amount of solvent be such that there is present about 0.5 to 10.0 ml of solvent per 100 ml of aqueous coupled collagen solution and most preferably about 1.0 ml of solvent per 100 ml of collagen solution.

Preferably, a large stoichiometric excess of the modifying agent is added to the collagen, due to the competitive hydrolysis of the modifying agent which occurs under the reaction conditions. The amount of modifying agent used must at least be sufficient to react with from 60 to 100 percent of the unreacted lysine epsilon amino groups and preferably enough to react with about 80 percent of the unreacted lysine epsilon amino groups. In as much as the hydrolysis of the modifying agent becomes increasingly dominant as the percentage of lysine amino groups declines, it is neither practical nor necessary to achieve 100 percent reaction. The amount of modifying agent necessary to react with at least 80 percent of the amino groups is dependent upon the reactivity of the modifying agent and the particular solvent, if any. For example, sulfonyl chlorides favor reaction with amines over hydrolysis. Therefore, less of the sulfonyl chlorides are required for the modification reaction than would be required with other modifying agents. Normally, however, at least 100 moles of modifying agent per mole of initial purified collagen, preferably at least 500 moles of modifying agent per mole of collagen and most preferably at least 750 moles of modifying agent per mole of collagen is required.

The reaction mixture is maintained throughout the reaction at a pH of preferably about 8 to 11, more preferably about 8.5 to 9.5, and most preferably about 9.0, by addition of a dilute base, e.g., 1N sodium hydroxide. The modification reaction is preferably substantially all of continued for at least thirty minutes in order to hydrolyze any unreacted modifying agent. As was the case for the coupling reaction, while the modification reaction can be conducted at a temperature of between about 0° and 35° C., it is preferably conducted at a temperature below about 20° C., preferably about 4° C., since reaction with amine groups is favored over hydrolysis at lower temperatures.

In most cases the pH of the reaction mixture is increased to at least 11.5 at the completion of the modification reaction to hydrolyze any unreacted modifying agent.

While what has been described thus far is a two-stage synthesis (first coupling of the collagen followed by modification of the remaining unreacted basic sites) a variation of this procedure is to conduct both the coupling and modification reactions simultaneously. In fact, with the more reactive coupling agents including dianhydrides such as 1,2,4,5-benzenetetracarboxylic dianhydride and bicyclo-(2,2,2)-oct-7-ene-2,3,5,6-tetracarboxylic-2,3,5,6-dianhydride; diacid halides such as succinyl chloride and 5-chlorosulfonyl-o-anisic acid chloride; and sulfonyl halides such as benzene trisulfonyl chloride and p-fluorosulfonyl benzenesulfonyl chloride, simultaneously reacting the collagen with the coupling agent and the modifying agent is preferred in order to prevent an unacceptably high degree of coupling in the resultant collagen product. When conducting the coupling and modification reactions simultaneously, one-half of the modifying agent (i.e., at least 50 moles per mole of initial purified collagen) is added to the reaction mixture, with the other half of the modifying agent being used to treat the coupled collagen product after coupling.

A still further variation for use with the more reactive coupling agents is to pre-react the purified collagen with approximately one-fourth of the modifying agent (i.e., at least about 25 moles per mole of initial purified collagen) prior to coupling. The remaining modifying agent is used to treat the collagen product after coupling.

IV. Modified Collagen Collection, Purification and Reconstitution

The modified collagen is precipitated by adjustment of the pH toward the isoelectric point. The precipitate is collected preferably by centrifugation and is washed with sterile pyrogen-free water to remove any excess reagents. The purified chemically-modified collagen is readied for use by reconstitution with enough physiological buffer and 1N NaOH to yield a 0.1 to 7.5, preferably 0.5 to 5.0 percent by weight solution of modified collagen at a pH of between 6.5 and 7.5, preferably 7.0 to 7.4. Suitable physiological buffers contain NaCl and optionally enough other salts such as KCl, $CaCl_2$, MgCl, $CH_3CO_2Na$, $NaH_2PO_4$, $Na_2HPO_4$ and sodium citrate to provide the buffer with an osmolarity of between about 200 and 400 mOs, preferably about 320 mOs. A preferred physiological buffer contains 0.64 percent by weight NaCl, 0.075 percent by weight KCl, 0.048 percent by weight $CaCl_2$, 0.030 percent by weight $MgCl_2$, 0.39 percent by weight $CH_3CO_2Na$ and 0.17 percent by weight $C_6H_5O_7Na_3$, and is commercially available as BSS ™ from Alcon Laboratories, Inc., Fort Worth, Tex. Preferably, for ophthalmic applications the buffer should also contain phosphate salts, e.g., $Na_2HPO_4$ and $NaH_2PO_4$. A more preferred phosphate buffered solution contains 0.84 percent by weight NaCl, 0.054 percent by weight KCl, 0.017 percent by weight $CaCl_2$, 0.028 percent by weight $Na_2HPO_4$ and 0.004 percent by weight $NaH_2PO_4$.

A final preferred step is to filter the reconstituted collagen through about a 10 micron filter to remove any particulates which may have accumulated during processing. The filtered collagen is then preferably stored under a positive nitrogen pressure, at a temperature of about 4° C. to avoid contamination.

When the preferred chemically-modified collagen fractions prepared according to this invention are dissolved in enough physiological buffer to provide a 1 to 5 percent by weight collagen solution they are
 (a) transparent and colorless with a transmission of about 100 percent from 400 to 700 nanometers and a refractive index approximately equal to that of water or the aqueous humor, i.e., about 1.33–1.40;
 (b) stable and collagen fiber free;
 (c) viscoelastic, i.e., exhibit the Weissenberg Effect (Introduction to Colloid and Surface Chemistry, London Butterworths, 1966);
 (d) pseudoplastic, having lower viscosities at higher shear rates;
 (e) thixotropic, i.e., recovers viscosity at rest after shear;
 (f) noninflammatory and biocompatible, with an ability to be absorbed into tissue fluid when injected into physiological tissue;
 (g) possessing a melt temperature of from about 32° C. to about 48° C.; and
 (h) possessing an osmolarity of about 260 to 340 mOs, preferably about 280 to 320 mOs.

All of the properties (a) through (h) of the collagen solution relate to its therapeutic activity in ocular use.

(a) Transparency

That the preferred collagen solutions for ocular use, i.e., up to 5 percent by weight chemically-modified collagen dissolved in physiological buffer, are transparent, colorless and have refractive indices approximately equal to the aqueous humor make them particularly appropriate as aqueous or vitreous replacements during intracapsular and extracapsular cataract extraction, intraocular lens implantation, corneal transplantation, and repair of retinal detachment. Transparency assures the surgeon that he/she can manipulate freely and maintain full control of the surgical procedure with complete and clear visibility in the presence of any quantity of the viscoelastic collagen solution.

(b) Stability

Physiological stability is defined as resistance to spontaneous fibrillogenesis at pH 7.2 and a temperature of 32°–42° C. Fibrillogenesis is defined as the self assembly of collagen molecules into insoluble aggregates. Collagen which has not been chemically-modified, as taught by the present invention, so as to react substantially all free amine groups is subject to spontaneous fibrillogenesis, for example, when dissolved in a physiological buffer and warmed to 37° C. nonchemically-modified collagen will spontaneously form a white opaque fibrous network. Resistance to fibrillogenesis means that the collagen solutions of the present invention will retain their clear transparent nature after insertion in the eye.

(c) Viscoelasticity

Collagen solutions of the invention exhibit what is known as the Weissenberg Effect, indicating that they are viscoelastic. The Weissenberg Effect describes the tendency in viscoelastic solutions for flow to occur at right angles to an applied force. When a rotating rod is lowered into a Newtonian (nonviscoelastic) liquid, the liquid is set into rotation and tends to move outwards, leaving a depression around the rod. When the rotating rod is lowered into a viscoelastic liquid, the liquid may actually climb up the rod. The rotation of the rod causes the liquid to be sheared circularly and, because of its elastic nature, it acts like a stretched rubber band tending to squeeze liquid in towards the center of the vessel and, therefore, up the rod.

The collagen solutions due to their viscoelastic character have lubricative properties which make them particularly useful as protective coatings on instruments and implants which are used near sensitive cellular and tissue surfaces. When used in the anterior chamber, the viscoelastic materials of this invention maintain anterior chamber depth and protect the corneal endothelium during intracapsular and extracapsular cataract lens extraction and during intraocular lens implantation. Yiscoelasticity is also important in vitreous surgery, in order that the solution be able to push back the retina to its normal position and not flow through the hole behind the retina. Furthermore, viscoelastic solutions provide long lasting support to the retina until it is healed, and maintain the rheological properties of the vitreous.

(d) Pseudoplasticity

The collagen solutions prepared according to this invention show significant viscosity decreases when subjected to increasing shear rates. The steady state viscosity of 2 percent by weight solutions of chemically-modified collagen in physiological buffer was measured using a cone and plate viscometer (commercially available as a Model 605 Mechanical Spectrometer from Rheometrics Co., Piscataway, N.J.) at a temperature between about 19° and 24° C. and at a humidity of about 50 percent. The steady state of viscosity was measured over a period of about 1.5 minutes. The viscosity of the collagen solutions was between about $0.15 \times 10^6$ and $4.0 \times 10^6$ centipoise at a shear rate of 0.10 seconds$^{-1}$; between about $0.20 \times 10^5$ and $7.5 \times 10^5$ centipoise at a shear rate of 1.0 seconds$^{-1}$; between about $0.3 \times 10^4$ and $1.0 \times 10^5$ centipoise at a shear rate of 10.0 seconds$^{-1}$; and between about $0.45 \times 10^3$ and $2.0 \times 10^4$ centipoise at a shear rate of 100.0 seconds$^{-1}$.

For ophthalmic applications a pseudoplastic material is ideal. At high shear stresses, i.e., during surgery when the eye tissues, instruments and/or implants are being manipulated within the eye, the viscosity of the material decreases thereby reducing the drag force on adjacent tissues, while at low shear stresses when the material is at rest the viscosity is high and the material acts as an effective lubricant for implants and/or for tissue surfaces which move relative to each other.

Additionally, pseudoplasticity permits the surgeon to move the collagen solution with relative ease through small bore needles and into small tissue spaces.

(e) Thixotropy

A thixotropic liquid may be defined as a pseudoplastic material which is able to regain its viscosity when allowed to rest for an extended period of time after being stressed. In general the chemically-modified collagen solutions of the present invention are able to regain their steady state viscosity after being injected through a syringe. Specifically, the collagen solutions regain 50 to 95 percent, preferably 65 to 95 percent of their steady state viscosity within about seven minutes after being sheared.

(f) Noninflammatory and Biologically Compatible

Preferred viscoelastic solutions of chemically-modified collagen in physiological buffer (about 1 to 3 percent by weight) were evaluated as anterior chamber implants in several animal species including rabbits, canine, swine, geese, and cynomologous monkeys. The chemically-modified collagen solutions were implanted in one eye and control materials such as air, balanced salt solution, e.g., BSS TM or Healon TM, commercially available from Pharmacia, were implanted in the contralateral eye. Both treated and control eyes were examined with a slit-lamp not more than 24 hours after implantation and again at 24 hour intervals up to 2 weeks. A modified McDonald-Shadduck score system (McDonald, T. O. and Shadduck, J.A. (1977). Eye Irritation. In: *Advances in Modern Toxicology*, vol. 4, *Dermatotoxicology and Pharmacology*, pp. 162–166. New York: John Wiley & Sons, Inc.) was used to evaluate the eyes. This system includes evaluation and scoring of conjunctival congestion, swelling and discharge, aqueous flare, iris inflammation, corneal cloudiness and edema, pannus formation, and anterior capsule appearance. In addition, evaluations of material present and extent of coverage in the anterior chamber were also made. Such evaluation indicated the overall equivalence or superiority of the chemically-modified collagen with air, BSS TM and Healon TM. Accordingly, the preferred collagen solutions were determined to be noninflammatory and biologically compatible.

(g) Melt Temperature

The melt temperature is that temperature at which the viscoelastic collagen solution exhibits a dramatic loss of viscosity, i.e., the viscosity in centipoise decreases over 100 to 1,000 fold when measured at a shear rate of 1 sec$^{-1}$. In general, the melt temperature of the collagen solutions prepared according to the present invention, (measured using a differential scanning calorimeter) is between about 32° C. and 48° C.

The melt temperature can be regulated by controlling the extent of coupling; a greater degree of coupling producing a material with a higher melt temperature. Collagen solutions which have a melt temperature of between about 34° C. and 38° C. are most suitable as anterior chamber implants for use in cataract extraction, IOL surgery and corneal transplants, and as viscoelastic surgical aids for corneal transplants. Lower melt temperature materials are preferred in these applications so that the material will clear from the eye relatively rapidly, i.e., within about twenty-four hours, thereby reducing the potential for a transient increase in intraocular pressure. Materials having a higher melt temperature of between about 39° C. and 45° C. are preferred in applications where a more thermally stable material is required, e.g., as a vitreous replacement, as a joint fluid replacement and as a viscoelastic surgical aid for corneal transplants.

(h) Osmolarity

The osmolarity of the collagen solution must not be so great or so little as to produce osmotic trauma to cells which come in contact with the solution. In general, the collagen solutions of the present invention are isotonic and have osmolarities of between about 200 and 400 mOs, preferably between about 260 and 340 mOs and most preferably between about 280 and 320 mOs.

The preferred collagen solutions of the present invention have particular applicability in ophthalmic surgery as an aqueous or vitreous replacement. The aqueous humor may be replaced by the collagen solution after various intraocular or extraocular surgical procedures in order to prevent cellular invasion of the anterior chamber, which would endanger the regeneration and function of the iris, ciliary body and corneal endothelium. The preferred collagen solution may also be used as a biological prosthesis in the anterior chamber after cataract surgery in order to push back prolapsed vitreous and, to provide separation between the vitreous and cornea. Further, the collagen solution could be used in the anterior chamber after keratoplasty to prevent adhesion formation between the corneal wound and the iris.

The preferred collagen solution may be implanted into the vitreous after extensive intravitreal surgery (removal of hemorrhages, opacities, etc.) to prevent excessive cellular reaction, and development of fibrous bands and preretinal tissue membranes.

Furthermore, the preferred collagen solutions of this invention are useful in retinal detachment surgery to provide a viscoelastic tool in the manipulation necessary for reattachment of the retina, to facilitate the intraocular wound healing by preventing excessive fibrous tissue formation and development of intravitreal scar tissue.

The preferred viscoelastic solutions of the present invention adhere to hydrophobic polymeric surfaces such as polymethylmethacrylate or polypropylene intraocular lenses. Thus, intraocular lenses can easily be coated with the collagen solution thereby causing less trauma and hazzard during insertion into the anterior or posterior chambers of the eye. The chemically-modified collagen could also be used as a wetting agent in contact lens solutions. Such a wetting solution would remain on the lens for a longer time than previously known wetting solutions, thereby prolonging the comfort afforded the lens wearer.

The collagen solutions would have use as a vehicle for medication in ophthalmic or orthopedic applications to prolong the effect of the drug.

Certain nonimmunogenic collagen solutions are useful in other therapeutic applications to prevent fibrous tissue formation and the consequent development of adhesion and scars. For example, in cases of traumatic arthritis, osteoarthritis and bursitis it is contemplated that nonimmunogenic collagen solutions can be used to replace the synovial fluid in a synovial space to impede the development of intraarticular fibrous tissue (pannus, ankylosis, adhesions) and to support the healing process of cartilage and synovial tissue. As used herein, the term "synovial space" is intended to mean that space which separates joints, tendons and/or bursae.

In anthroplasty, osteotomy and all types of intraarticular surgery, such as arthroscopy, certain collagen solutions of the invention could be used to protect the articular cartilage surfaces from postoperative injury and from the possible harmful effect of prosthetic surfaces, to prevent excess fibrous tissue formation and to promote the normal healing of the soft tissues and cartilage.

It is further contemplated that certain collagen solutions of the present invention could be implanted between tendons and their sheaths to minimize adhesion formation after any surgical procedure or around peripheral nerves and nerve roots after injury or surgery when damage to the connective tissue around the nerve is extensive and excessive scar formation is expected. Implantation of the collagen solutions around the healing (regenerating) nerve may protect it from invasion by connective tissue cells.

In order to prevent adhesion formation between two endothelial or connective tissue membranes, certain collagen solutions could be implanted between mesothelial, pericardial and pleural sheets.

The chemically-modified collagen of the present invention when in a dry membrane form would also be useful as a wound dressing. The collagen can act as a barrier to water and microorganisms when used to cover skin wounds.

Certain collagen solutions could be used to separate tissue surfaces. The viscoelastic properties of the solution would protect the tissue during surgical manipulation and postoperatively. The collagen solutions would be beneficial in improving the gliding function of muscle sheaths and tendon sheaths in traumatic injuries.

In orthopedic or cardiovascular surgery certain collagen solutions would be useful to lubricate and coat implants. Further, the solution could be used to prevent vascular grafts from contacting body fluids, and could also be used as a component of synthetic vessels.

Furthermore, the collagen solutions of the present invention would be useful as moisturizers and lubricants in cosmetic creams and lotion.

Lyophilized, coupled collagen and coupled and amine-modified collagen solutions of this invention are useful as hemostatic agents.

Insoluble, coupled collagen having a pH of 7 and coupled and amine-modified collagen materials of the present invention can be used for soft tissue augmentation.

Other uses of the chemically-coupled and/or amine-modified collagen compounds and viscoelastic solutions of the invention will undoubtedly occur to those skilled in the art and thus, the foregoing description does not limit the possible applications.

In order more clearly to disclose the nature of the present invention, the following examples illustrating compositions in accordance with the invention and methods of using such compositions will now be described. It should be understood, however, that this is done solely by way of example and is intended neither to delineate the scope of the invention nor limit the ambit of the appended claims.

EXAMPLE 1

Isolation and purification of collagen Type I was accomplished by the following method. Clean dehaired bovine hide (200 g) was cryopulverized and added to 15 liters 0.5M acetic acid solution at 4° C. The collagen was allowed to solubilize for 1 hour. The terminal non-helical portions of the telopeptide collagen molecules were cleaved from the helical portions of the molecule by adding pepsin (5.86 g) to the collagen solution and agitating this mixture at 4° C. for 16 hours. The pH of the solution was then increased to 7.0 by addition of 10 N sodium hydroxide. After 2 hours of mixing (while maintaining the temperature at 4° C.) the denatured pepsin was removed from solution by filtration. The collagen solution was then made 2.5M in sodium chloride by gradual addition of the solid salt. The resultant collagen precipitate was collected and reconstituted in 0.5 M acetic acid. The collagen was again precipitated by addition of sodium chloride to 0.8 M. The precipitate was collected and reconstituted in 0.5 M acetic acid. Precipitation of the collagen by addition of sodium chloride to 0.8 M was repeated. The precipitate collected was reconstituted in 0.1 M acetic acid to provide a high purity 0.3 percent wt/wt collagen Type I solution having a pH of about 3.

The filter-sterilized purified collagen was chemically modified in the following manner. All reactions were conducted under aseptic conditions using sterile solutions and reagents. The collagen solution (3000 ml) was treated with 5N sodium hydroxide at 4° C. to raise the pH to 9.0. Finely-divided succinic anhydride powder (1.60 g) was added to this solution. The solution was vigorously agitated and the pH was maintained at 9.0±0.25 by gradual addition of 1N sodium hydroxide. After about two minutes, succinyl chloride (0.60 g) was added. Agitation was continued for 30 minutes and the pH was maintained at 9.0±0.25 by addition of 1N sodium hydroxide. The resultant coupled collagen product was further treated (at 24° C.) by addition of finely-divided succinic anhydride (1.60 g). As before, the pH was maintained at 9.0±0.25 by gradual addition of 1N sodium hydroxide. The solution was agitated for an additional 60 minutes. The pH was decreased to 4.1 by addition of 6N HCl in order to precipitate the chemically-modified collagen product. The product was collected by centrifugation and washed successively with four volumes of sterile water. The collagen precipitate was dissolved in a phosphate-buffered solution[1] to provide a 2 percent by weight modified collagen solution and the pH was adjusted to 7.2 with 1N sodium hydroxide.

The phosphate-buffered solution contained 0.84 percent by weight NaCl, 0.054 percent by weight KCL, 0.017 percent by weight $CaCl_2$, 0.028 percent by weight $Na_2HPO_4$, and 0.004 percent by weight $NaH_2PO_4$.

The collagen solution was colorless and transparent by both visual inspection and light/optical microscopy at 40x.

The chemically-modified collagen solution was evaluated as an anterior chamber implant in New Zealand white rabbits, inbred beagle dogs, domestic white geese, Yorkshire pigs and cynomologous monkeys. Implantation was conducted as follows. The animal was anesthetized intramuscularly with ketamine. After sedation, the orbital areas were shaved and the animal was moved to surgery and anesthesized using halothane and nitrous oxide. The eyes were coated with chloromycetin and betadine was applied to the surrounding areas. The eyes were lavaged with BSS TM. The orbital areas were allowed to dry and a speculum was placed in the eye. All surgical procedures were performed using ophthalmomicrosurgery.

An incision approximately 1 mm was made into the anterior chamber at the limbus using a Supersharp Beaver TM Blade. Aqueous fluid drained and the aqueous chamber was irrigated with BSS TM or BSS TM containing heparin (1 cc of 5000 units/cc in 500 ml) and epinephrine (1 cc of 1:1000 in 500 ml). The anterior chamber was aspirated and completely deflated. The chamber was then filled using a 27-gauge cannula with the chemically-modified collagen (a 2 percent by weight solution in phosphate-buffered solution[2]). Contralateral control eyes were filled with BSS TM, air, or a solution of viscoelastic sodium hyaluronate, commercially available as Healon TM from Pharmacia Co. The quantity of material injected into the anterior chamber was dependent upon the aqueous volume and the inherent intraocular pressure. Material was injected until back pressure forced it out of the injection site.

The phosphate-buffered solution contained 0.84 percent by weight NaCl, 0.054 percent by weight KCl, 0.017 percent by weight $CaCl_2$, 0.028 percent by weight $Na_2HPO_4$, and 0.004 percent by weight $NaH_2PO_4$.

Both treated and control eyes were evaluated by a slit-lamp microscope using the McDonald-Shadduck system at not more than 24 hours after treatment and again at 24 hour intervals up to 96 hours. This system includes evaluation and scoring of conjunctival congestion, swelling and discharge, aqueous flare, iris inflammation, corneal cloudiness and edema, pannus formation and anterior capsule appearance. Such evaluation indicated overall superiority of the chemically-modified collagen made according to this example to air, BSS TM, and Healon TM.

Chemically-modified collagen (a 2 percent by weight solution in a phosphate-buffered solution[2]) prepared according to this Example 1 was evaluated as an anterior adjunct during intraocular lens implantation in a New Zealand white rabbit. It was observed that the collagen solution maintained inflation of the anterior chamber for at least 30 minutes and provided excellent chamber depth suitable for extraction of the cataract lens and implantation of an intraocular lens (IOL). IOL insertion was facilitated while traumatic damage, as observed during IOL insertion without use of a viscoelastic material, was reduced. The collagen material coated the surgical instruments and the surfaces of the IOL.

In order to test the biocompatibility of the modified collagen solution the following test was performed. Primary human endothelial cell cultures were maintained on multiwell plates coated with 1 percent gelatin in normal saline (0.9 percent NaCl). After reaching confluency the cells were washed with normal saline and were flooded with the chemically-modified collagen solution (2 percent by weight in phosphate-buffered solution[3]). After one hour at 35.5° C. the collagen solution was aspirated and the cells were rinsed with serum-free media. The cells were incubated in the medium for an additional 24 hours. The cell cultures were examined by phase contrast microscopy before application of the collagen solution, 3 minutes after application of the collagen solution, one hour after application of the collagen and 24 hours after removal of the collagen solution. The treated cells were as healthy (i.e., had not died or undergone morphological changes) as those which were untreated, indicating that the collagen solution had no toxic effects.

The phosphate-buffered solution contained 0.84 percent by weight NaCl, 0.054 percent by weight KCL, 0.017 percent by weight $CaCl_2$, 0.028 percent by weight $Na_2HPO_4$, and 0.004 percent by weight $NaH_2PO_4$.

The collagen solution (2 percent by weight in phosphate-buffered solution3) was shown to be viscoelastic, i.e., exhibit the Weissenberg Effect, using the following test. A motor-driven one-half inch impeller diameter polytetrafluoroethylene-coated stirring rod was inserted into a 50 ml beaker containing about 30 ml of the collagen solution, and was rotated at about 40 revolutions per minute. The collagen solution flowed at right angles to the applied force and moved up the stirring rod at least 0.5 cm.

The viscosity of the collagen solution (2 percent by weight in phosphate-buffered solution[3]) was examined rheometrically as follows. Viscosity measurements were taken at room temperature (22°-24° C.) with a mechanical spectrometer (commercially available as a Model 605 Mechanical Spectrometer from Rheometrics Co., Piscataway, New Jersey) using the cone and plate technique. The angle of the cone was maintained at 0.1 radians, and the sample was sheared for 30 seconds to allow equilibration before the force was measured over a period of 1.5 minutes and the viscosity was determined. viscosities were determined in this manner at several shear rates and are reported in Table I.

The phosphate-buffered solution contained 0.84 percent by weight NaCl, 0.054 percent by weight KCL, 0.017 percent by weight CaCl$_2$, 0.028 percent by weight Na$_2$HPO$_4$, and 0.004 percent by weight NaH$_2$PO$_4$.

TABLE I

| Shear Rates (in sec$^{-1}$) | Viscosity (in centipoise) |
| --- | --- |
| 100.0 | 4,215 |
| 10.0 | 10,280 |
| 1.0 | 65,200 |
| 0.1 | 370,500 |

The viscosity of the collagen solution decreases with increasing shear rates indicating that the solution is pseudoplastic.

The thixotropy of the collagen solution (2 percent by weight in phosphate-buffered solution[4]) was demonstrated as follows: Viscosity measurements at a shear rate of 0.1 sec$^-$ were determined using the cone and plate technique described above. After shear thinning at 500 sec$^-$ for 30 seconds, the shear force was removed and the sample was permitted to relax for 7 minutes. The sample was sheared again at a shear rate of 0.1 sec$^-$ and the viscosity again recorded. The results are reported in Table II.

The phosphate-buffered solution contained 0.84 percent by weight NaCl, 0.054 percent by weight KCL, 0.017 percent by weight CaCl$_2$, 0.028 percent by weight Na$_2$HPO$_4$, and 0.004 percent by weight NaH$_2$PO$_4$.

TABLE II

| Initial Viscosity at 0.1 sec$^{-1}$ (in centipoise) | Viscosity After 7 Minutes Recovery at 0.1 sec$^{-1}$ (in centipose) | Percent Recovery |
| --- | --- | --- |
| 370,500 | 266,760 | 72 |

The collagen solution (about 2 percent by weight in BSS ™) was also tested for efficacy as an anterior chamber replacement using the following test, referred to hereinafter as the "syringe test." A 250 microliter glass syringe barrel (Model 1725RN available from Hamilton Co., Reno, Nev.) was equipped with a plunger from the Model 1725N syringe also available from Hamilton Co. A brass weight was threaded to the top of the plunger to exert a constant force of 64 grams. The teflon tip of the plunger was gently abraded with 30 micron grit lapping paper until the plunger moved freely. The barrel was fitted with a 2-inch 22 gauge removable needle. The collagen solution was introduced into the barrel bubble-free by using a needleless 1 ml plastic tuberculin syringe. The time to extrude 0.05 ml of solution, i.e. the time for the plunger to travel 0.5 in. down the barrel, was recorded in Table III.

TABLE III

| Sample | Collagen Concentration (Percent by Weight) | Extrusion Time (sec) |
| --- | --- | --- |
| 1 | 2.06 | 20 |
| 2 | 2.11 | 19 |
| 3 | 2.24 | 31 |
| 4 | 2.13 | 26 |

Applicants have determined that in order to adequately maintain the anterior chamber of the eye an extrusion time greater than about 20 sec. is required. Additionally, in order for the solution to pass out of the eye an extrusion time of less than about 120 sec. is required. Preferably, the extrusion time is between about 20 and 40 seconds.

The melt temperature of the 2 percent collagen solution as determined by Differential Scanning Calorimetry was about 35° to 36° C.

EXAMPLE 2

Chemically-modified collagen is prepared according to the procedure of Example 1 except that phthalic anhydride (2.35 g) is used in place of succinic anhydride (1.60 g) wherever succinic anhydride was used.

The collagen solution is colorless and transparent as determined by both visual inspection and light/optical microscopy at 40x.

The collagen solution (2 percent by weight in a phosphate-buffered solution[5]) is evaluated as an anterior chamber implant in New Zealand white rabbits using the McDonald-Shadduck system in accordance with the procedure described in Example 1. Such evaluation indicates overall equivalence or superiority of the chemically-modified collagen of this example with air, BSS ™ and Healon ™.

The phosphate-buffered solution contained 0.84 percent by weight NaCl, 0.054 percent by weight KCL, 0.017 percent by weight CaCl$_2$, 0.028 percent by weight Na$_2$HPO$_4$, and 0.004 percent by weight NaH$_2$PO$_4$.

The collagen solution (about 2 percent by weight in phosphate buffered solution[5]) exhibits the Weissenberg Effect when tested in accordance with the procedure described in Example 1. The collagen solution is pseudoplastic, exhibiting decreasing viscosities at increasing shear rates when tested in accordance with the procedure of Example 1. The collagen solution is thixotropic, recovering about 65-95 percent of its initial viscosity within 7 minutes of shearing at 0.1 sec$^{-1}$.

The phosphate-buffered solution contained 0.84 percent by weight NaCl, 0.054 percent by weight KCl, 0.017 percent by weight CaCl$_2$, 0.028 percent by weight Na$_2$HPO$_4$, and 0.004 percent by weight NaH$_2$PO$_4$.

The melt temperature of the 2 percent collagen solution as determined by Differential Scanning Calorimetry is about 34° to 37° C.

EXAMPLE 3

Purified Type I collagen was prepared according to the procedure described in Example 1 except that the purified collagen precipitate was reconstituted in 1700 ml·0.05 M acetic acid to provide a 0.15 percent wt/wt collagen solution. This solution was maintained at 4° C. and treated with 10N sodium hydroxide to raise the pH to 5. To this vigorously agitated solution terephthaloyl chloride (0.1036 g) in 17 ml N,N'-dimethylformamide was added all at once. The pH of the stirring mixture was rapidly brought to 9.0±0.25 with 5 N sodium hydroxide. Overshoot was corrected by back-addition of 6 N HCl. Stirring was continued for 6 minutes while the pH was maintained at 9.0. The pH was raised to 11.5 for 2 minutes and then returned again to 9.0 by additions of 5N NaOH and 6N HCl, respectively in order to hydrolize the unreacted terephthaloyl chloride, thereby producing the coupled collagen product.

To the coupled collagen product maintained at 4° C., glutaric anhydride (0.1455 g) in 17 ml of acetone was added dropwise while stirring. The pH was maintained at 9.0±0.25 with 1 N sodium hydroxide. The solution was agitated for an additional 14 minutes. The pH was taken to 11.8 with 1 N sodium hydroxide for 2 minutes and was then returned to 9.0 with 6N HCl for 15 minutes. The pH of the solution was then dropped to 4.1 by addition of 6N HCl to precipitate the chemically-modified collagen product. The product was collected by centrifugation and washed as in Example 1. The modified collagen precipitate was dissolved in BSS TM to provide a 2 percent by weight modified collagen solution, and the pH was adjusted to 7.15 with 1 N sodium hydroxide.

This solution was colorless and transparent as determined by both visual inspection and light/optical microscopy at 40x.

viscosity as a function of shear rate was measured in accordance with the procedure described in Example 1, with the following results.

TABLE IV

| Shear Rate (1/sec) | Viscosity (cp) |
| --- | --- |
| 100.0 | 2,750 |
| 10.0 | 9,847 |
| 1.0 | 61,490 |
| 0.1 | 425,000 |

Viscosity decreased as shear rate increased indicating that the 2 percent by weight collagen solution was pseudoplastic.

Chemically-modified collagen (a 2 percent by weight solution in BSS TM) was evaluated as an anterior chamber implant in New Zealand white rabbits. The collagen solution maintained inflation of the anterior chamber for at least 30 minutes and provided excellent chamber depth suitable for extraction of the cataract lens and implantation of an intraocular lens (IOL). The collagen solution coated the surgical instruments and intraocular lenses.

The collagen solution (2 percent by weight in a phosphate-buffered solution[6]) was evaluated as an anterior chamber implant in New Zealand white rabbits using the McDonald-Shadduck system in accordance with the procedure described in Example 1. Such evaluation indicated overall equivalence or superiority of the chemically-modified collagen of this example with air, BSS TM and Healon TM.
The phosphate-buffered solution contained 0.84 percent by weight NaCl, 0.054 percent by weight KCl, 0.017 percent by weight CaCl$_2$, 0.028 percent by weight Na$_2$HPO$_4$, and 0.004 percent by weight NaH$_2$PO$_4$.

The biocompatibility of the collagen solution was tested as follows. Decontaminated human corneas having less than 5 percent cell death were incubated for 4 days at 34° C. in media containing BSS TM, collagen solution (2 percent by weight in BSS TM) 25 percent by volume in BSS TM or collagen solution (2 percent by weight in BSS TM) 50 percent by volume in BSS TM. After incubation the corneas were stained with trypan blue or atya alizarin red and examined for cell morphology and density. Corneas treated with the collagen solutions were not significantly different from corneas treated with BSS TM.

The collagen solution (about 2 percent by weight in BSS TM) exhibited the Weissenberg Effect when tested in accordance with the procedures described in Example 1.

The thixotropy of the 2 percent collagen solution was determined as described in Example 1. The results are reported in Table v.

TABLE V

| Initial Viscosity at 0.1 sec$^{-1}$ (in centipoise) | Viscosity After 7 Minutes Recovery at 0.1 sec$^{-1}$ (in centipoise) | Percent Recovery |
| --- | --- | --- |
| 425,000 | 308,100 | 72 |

The melt temperature of the 2 percent collagen solution as determined by Differential Scanning Calorimetry was about 39° to 40° C.

EXAMPLE 4

Chemically-modified collagen was prepared according to the procedure of Example 3 except that diglycolic anhydride (0.124 g) in 17 ml of acetone was used in place of glutaric anhydride as the amine modifier.

The collagen solution was colorless and transparent as determined by both visual inspection and light/optical microscopy at 40x.

The collagen solution (2 percent by weight in a phosphate-buffered solution[7]) is evaluated as an anterior chamber implant in New Zealand white rabbits using the McDonald-Shadduck system in accordance with the procedure described in Example 1. Such evaluation indicates overall equivalence or superiority of the chemically-modified collagen made according to this example with air, BSS TM and Healon TM.
The phosphate-buffered solution contained 0.84 percent by weight NaCl, 0.054 percent by weight KCl, 0.017 percent by weight, CaCl$_2$, 0.028 percent by weight Na$_2$HPO$_4$, and 0.004 percent by weight NaH$_2$PO$_4$.

The collagen solution (about 2 percent by weight in BSS TM) exhibits the Weissenberg Effect when tested in accordance with the procedure described in Example 1. The collagen solution is pseudoplastic, exhibiting decreasing viscosities at increasing shear rates when tested in accordance with the procedure of Example 1. The collagen solution is thixotropic, recovering about 65-95 percent of its initial viscosity within 7 minutes of shearing at 0.1 sec$^{-1}$.

The melt temperature of the 2 percent collagen solution as determined by Differential Scanning Calorimetry is about 34° to 37° C.

EXAMPLE 5

Chemically-modified collagen was prepared according to the procedure of Example 3 except that 1,2,4-benzenetricarboxylic anhydride (0.425 g) was used in place of the glutaric anhydride as the amine modifier. After precipitation and washing, the collagen was dissolved in BSS TM to provide a 2 percent by weight collagen solution. The pH of the solution was adjusted to 7.2 with 1 N sodium hydroxide.

The collagen solution was colorless and transparent as determined by both visual inspection and light/optical microscopy at 40x.

The collagen solution was evaluated as in an anterior chamber implant in New Zealand white rabbits. The collagen solution maintained inflation of the anterior chamber for at least 30 minutes and provided excellent chamber depth suitable for extraction of the cataract lens and implantation of an intraocular lens (IOL).

The collagen solution (2 percent by weight in BSS TM) was evaluated as an anterior chamber implant in adult cats in accordance with the procedure described in Example 1. The eyes were examined 24 and 48 hours post-operatively by specular microscopy to evaluate general morphology and density of endothelial cells. No adverse effects on the corneal endothelium were observed.

The collagen solution (2 percent by weight in a phosphate-buffered solution[8]) was evaluated as an anterior chamber implant in New Zealand white rabbits using the McDonald-Shadduck system in accordance with the procedure described in Example 1. Such evaluation indicated overall equivalence or superiority of the chemically-modified collagen of this example with air, BSS TM and Healon TM.

The phosphate-buffered solution contained 0.84 percent by weight NaCl, 0.054 percent by weight KCl, 0.017 percent by weight $CaCl_2$, 0.028 percent by weight $Na_2HPO_4$, and 0.004 percent by weight $NaH_2PO_4$.

The collagen solution (about 2 percent by weight in BSS TM) exhibits the Weissenberg Effect when tested in accordance with the procedure described in Example 1. The collagen solution is pseudoplastic, exhibiting decreasing viscosities at increasing shear rates when tested in accordance with the procedure of Example 1. The collagen solution is thixotropic, recovering about 75 percent of its initial viscosity within 7 minutes of shearing at 0.1 sec$^{-1}$.

The melt temperature of the 2 percent collagen solution as determined by Differential Scanning Calorimetry is about 35° to 36° C.

EXAMPLE 6

Chemically-modified collagen was prepared according to the procedure of Example 3 except that cyclopentanetetracarboxylic dianhydride (0.1786 g) in 17 ml of N-methyl pyrrolidone was used in place of terephthaloyl chloride as the coupler, and 1,2,4-benzenetricarboxylic anhydride (0.5667 g) in 17 ml of acetone was used in place of glutaric anhydride as the amine modifier.

The collagen solution was colorless and transparent as determined by both visual inspection and light/optical microscopy at 40x.

The collagen solution (2 percent by weight in a phosphate-buffered solution[9]) is evaluated as an anterior chamber implant in New Zealand white rabbits using the McDonald-Shadduck system in accordance with the procedure described in Example 1. Such evaluation indicates overall equivalence of the chemically-modified collagen made according to this example with air, BSS TM and Healon TM.

The phosphate-buffered solution contained 0.84 percent by weight NaCl, 0.054 percent by weight KCl, 0.017 percent by weight $CaCl_2$, 0.028 percent by weight $Na_2HPO_4$, and 0.004 percent by weight $NaH_2PO_4$.

The collagen solution (about 2 percent by weight in BSS TM) exhibits the Weissenberg Effect when tested in accordance with the procedure described in Example 1. The collagen solution is pseudoplastic, exhibiting decreasing viscosities at increasing shear rates when tested in accordance with the procedure of Example 1. The collagen solution is thixotropic, recovering about 65–95 percent of its initial viscosity within 7 minutes of shearing at 0.1 sec$^{-1}$.

The melt temperature of the 2 percent collagen solution as determined by Differential Scanning Calorimetry is about 34° to 37° C.

EXAMPLE 7

Chemically-modified collagen was prepared according to the procedure of Example 3 except that sebacoyl chloride (0.2033 g) in 17 ml of N-methyl pyrrolidone was used in place of terephthaloyl chloride as the coupler and succinic anhydride (0.1063 g) in 17 ml of N-methyl pyrrolidone was used in place of glutaric anhydride as the amine modifier.

The collagen solution (2 percent by weight in a phosphate-buffered solution[9]) is evaluated as an anterior chamber implant in New Zealand white rabbits using the McDonald-Shadduck system in accordance with the procedure described in Example 1. Such evaluation indicates overall equivalence or superiority of the chemically-modified collagen made according to this example with air, BSS TM and Healon TM.

The phosphate-buffered solution contained 0.84 percent by weight NaCl, 0.054 percent by weight KCl, 0.017 percent by weight $CaCl_2$, 0.028 percent by weight $Na_2HPO_4$, and 0.004 percent by weight $NaH_2PO_4$.

The collagen solution (about 2 percent by weight in BSS TM) exhibits the Weissenberg Effect when tested in accordance with the procedure described in Example 1. The collagen solution is pseudoplastic, exhibiting decreasing viscosities at increasing shear rates when tested in accordance with the procedure of Example 1. The collagen solution is thixotropic, recovering about 73 percent of its initial viscosity within 7 minutes of shearing at 0.1 sec$^{-1}$.

The melt temperature of the 2 percent collagen solution as determined by Differential Scanning Calorimetry is about 34° to 37° C.

EXAMPLE 8

Chemically-modified collagen was prepared according to the procedure of Example 3 except that 4-[p-(o-chlorocarbonyl benzoyl)phenyl]butyryl chloride (0.2652 g) in 17 ml of acetone was used in place of terephthaloyl chloride as the coupler and succinic anhydride (0.3933 g) in 17 ml of acetone was used in place of glutaric anhydride as the amine modifier.

The collagen solution (2 percent by weight in a phosphate-buffered solution[10]) is evaluated as an anterior chamber implant in New Zealand white rabbits using the McDonald-Shadduck system in accordance with the procedure described in Example 1. Such evaluation indicates overall equivalence of the chemically-modified collagen made according to this example with air, BSS TM and Healon TM.

The phosphate-buffered solution contained 0.84 percent by weight NaCl, 0.054 percent by weight KCl, 0.017 percent by weight $CaCl_2$, 0.028 percent by weight $Na_2HPO_4$, and 0.004 percent by weight $NaH_2PO_4$.

The collagen solution (about 2 percent by weight in BSS TM) exhibits the Weissenberg Effect when tested in accordance with the procedure described in Example 1. The collagen solution is pseudoplastic, exhibiting decreasing viscosities at increasing shear rates when tested in accordance with the procedure of Example 1. The collagen solution is thixotropic, recovering about 65 to 95 percent of its initial viscosity within 7 minutes of shearing at 0.1 sec$^{-1}$.

The melt temperature of the 2 percent collagen solution as determined by Differential Scanning Calorimetry is about 34° to 37° C.

EXAMPLE 9

Chemically-modified collagen was prepared according to the procedure of Example 3 except that diglycolic diacid chloride (0.1442 g) in 17 ml of acetone was used in place of terephthaloyl chloride as the coupler and diglycolic anhydride (0.1973 g) in 17 ml of acetone was used in place of glutaric anhydride as the amine modifier.

The collagen solution (2 percent by weight in a phosphate-buffered solution[10]) is evaluated as an anterior chamber implant in New Zealand white rabbits using the McDonald-Shadduck system in accordance with the procedure described in Example 1. Such evaluation indicates overall equivalence or superiority of the chemically-modified collagen made according to this example with air, BSS TM and Healon TM.

The collagen solution (about 2 percent by weight in BSS TM) exhibits the Weissenberg Effect when tested in accordance with the procedure described in Example 1. The collagen solution is pseudoplastic, exhibiting decreasing viscosities at increasing shear rates when tested in accordance with the procedure of Example 1. The collagen solution is thixotropic, recovering about 65 to 95 percent of its initial viscosity within 7 minutes of shearing at 0.1 sec$^{-1}$.

The melt temperature of the 2 percent collagen solution as determined by Differential Scanning Calorimetry is about 34° to 37° C.

EXAMPLE 10

Purified Type I collagen, prepared as in Example 3 (1700 ml of a 0.15 percent wt/wt collagen solution in 0.05 M acetic acid), was treated at 4° C. with 10 N sodium hydroxide to raise the pH to 5.0. A solution of bicyclo-(2,2,2)-oct-7-ene-2,3,5,6-tetracarboxylic-2,3,5,6-dianhydride (0.0810 g) and 1,2,4-benzenetricarboxylic anhydride (0.0660 g) in 17 ml of N,N-dimethylformamide was added all at once to the purified Type I collagen with stirring. The pH was immediately increased to 9.4 using 10 N sodium hydroxide, and the solution was stirred for 10 minutes while maintaining the pH at 9.4 by gradual addition of 1 N sodium hydroxide. After 10 minutes the pH was increased to 12.1 by addition of 10 N sodium hydroxide, and the pH was maintained at 12.1 for 2 minutes. The pH was then decreased to 9.0 by addition of 6 N HCl and maintained at this pH for 10 minutes while the temperature of the solution was increased from 4° C. to 32° C.

To this coupled collagen product 1,2,4-benzenetricarboxylic anhydride (0.2472 g) in 17 ml acetone was added dropwise, along with 1 N sodium hydroxide to maintain the pH at 9.0±0.25. After addition was complete the solution was agitated for 10 minutes. The pH was increased to 12.5 for 3 minutes and decreased to 9.0 using 10 N NaOH and 6 N HCl, respectively. After 10 minutes of agitation at pH 9.0, the pH was reduced to 3.2 and the chemically-modified collagen product precipitated. The solution was agitated mildly for 15 minutes to ensure complete precipitation. The material was collected by centrifugation and the collected precipitate was washed successively four times with sterile water at a dilution of 10 parts water to 1 part wet precipitate.

A 2 percent by weight solution of the collagen in BSS TM was colorless and transparent as determined by both visual inspection and light/optical microscopy at 40x.

The collagen solution (2 percent by weight in BSS TM) was evaluated as an anterior chamber implant in New Zealand white rabbits using the McDonald-Shadduck system in accordance with the procedure described in Example 1. Such evaluation indicated overall equivalence or superiority of the chemically-modified collagen made according to this example with air, BSS TM and Healon TM.

The collagen solution (about 2 percent by weight in BSS TM) exhibits the Weissenberg Effect when tested in accordance with the procedure described in Example 1. The collagen solution is pseudoplastic, exhibiting decreasing viscosities at increasing shear rates when tested in accordance with the procedure of Example 1. The collagen solution is thixotropic, recovering about 65 to 95 percent of its initial viscosity within 7 minutes of shearing at 0.1 sec$^{-1}$.

The melt temperature of the 2 percent collagen solution as determined by Differential Scanning Calorimetry is about 34° to 37° C.

EXAMPLE 11

Chemically-modified collagen was prepared according to the procedure of Example 10 except that 1,3,5-benzenetrisulfonyl chloride (0.0727 g) in 17 ml N-methyl-pyrrolidone was used in place of bicyclo-(2,2,2)-oct-7-ene-2,3,5,6-tetracarboxylic-2,3,5,6-dianhydride as the coupler, and o-sulfobenzoic acid cyclic anhydride (0.0718 g) in 17 ml acetone was used in place of 1,2,4-benzenetricarboxylic anhydride as the amine modifier.

A 2 percent by weight solution of the collagen in BSS TM was colorless and transparent as determined by both visual inspection and light/optical microscopy at 40 x.

The collagen solution (2 percent by weight in a phosphate-buffered solution[11]) is evaluated as an anterior chamber implant in New Zealand white rabbits using the McDonald-Shadduck system in accordance with the procedure described in Example 1. Such evaluation indicates overall equivalence of the chemically-modified collagen made according to this example with air, BSS TM and Healon TM.

[11] The phosphate-buffered solution contained 0.84 percent by weight NaCl, 0.054 percent by weight KCl, 0.017 percent by weight CaCl$_2$, 0.028 percent by weight Na$_2$HPO$_4$, and 0.004 percent by weight NaH$_2$PO$_4$.

The collagen solution (about 2 percent by weight in BSS TM) exhibits the Weissenberg Effect when tested in accordance with the procedure described in Example 1. The collagen solution is pseudoplastic, exhibiting decreasing viscosities at increasing shear rates when tested in accordance with the procedure of Example 1. The collagen solution is thixotropic, recovering about 75 to 95 percent of its initial viscosity within 7 minutes of shearing at 0.1 sec$^{-1}$.

The melt temperature of the 2 percent collagen solution as determined by Differential Scanning Calorimetry is about 35° to 42° C.

EXAMPLE 12

Chemically-modified collagen was prepared according to the method of Example 10 except that 3,3',4,4'-benzophenonetetracarboxylic dianhydride (0.10 g) was used in place of bicyclo-(2,2,2)-oct-7-ene-2,3,5,6-tetracarboxylic dianhydride as the coupling agent.

A 2 percent by weight solution of the collagen in BSS TM was colorless and transparent as determined by both visual inspection and light/optical microscopy at 40 x.

The collagen solution (2 percent by weight in a phosphate-buffered solution[11]) is evaluated as an anterior chamber implant in New Zealand white rabbits using the McDonald-Shadduck system in accordance with the procedure described in Example 1. Such evaluation indicates overall equivalence or superiority of the chemically-modified collagen made according to this example with air, BSS TM and Healon TM.

[11] The phosphate-buffered solution contained 0.84 percent by weight NaCl, 0.054 percent by weight KCl, 0.017 percent by weight $CaCl_2$, 0.028 percent by weight $Na_2HPO_4$, and 0.004 percent by weight $NaH_2PO_4$.

The collagen solution (about 2 percent by weight in BSS TM) exhibits the Weissenberg Effect when tested in accordance with the procedure described in Example 1. The collagen solution is pseudoplastic, exhibiting decreasing viscosities at increasing shear rates when tested in accordance with the procedure of Example 1. The collagen solution is thixotropic, recovering about 65 to 95 percent of its initial viscosity within 7 minutes of shearing at 0.1 $sec^{-1}$.

The melt temperature of the 2 percent collagen solution as determined by Differential Scanning Calorimetry is about 34° to 37° C.

EXAMPLE 13

Chemically-modified collagen was prepared according to the procedure of Example 10 except that 1,2,4,5-benzenetetracarboxylic dianhydride (0.0203 g) was used in place of bicyclo-(2,2,2)-oct-7-ene-2,3,5,6-tetracarboxylic-2,3,5,6-dianhydride as the coupling agent, and only 0.1674 g of the amine modifier benzenetricarboxylic anhydride was used.

A 2 percent by weight solution of the collagen in BSS TM was colorless and transparent as determined by both visual inspection and light/optical microscopy at 40 x.

The collagen solution (2 percent by weight in a phosphate-buffered solution[12]) is evaluated as an anterior chamber implant in New Zealand white rabbits using the McDonald-Shadduck system in accordance with the procedure described in Example 1. Such evaluation indicates overall equivalence or superiority of the chemically-modified collagen made according to this example with air, BSS TM and Healon TM.

[12] The phosphate-buffered solution contained 0.84 percent by weight NaCl, 0.054 percent by weight KCl, 0.017 percent by weight $CaCl_2$, 0.028 percent by weight $Na_2HPO_4$, and 0.004 percent by weight $NaH_2PO_4$.

The collagen solution (about 2 percent by weight in BSS TM) exhibits the Weissenberg Effect when tested in accordance with the procedure described in Example 1. The collagen solution is pseudoplastic, exhibiting decreasing viscosities at increasing shear rates when tested in accordance with the procedure of Example 1. The collagen solution is thixotropic, recovering about 65 to 95 percent of its initial viscosity within 7 minutes of shearing at 0.1 $sec^{-1}$.

The melt temperature of the 2 percent collagen solution as determined by Differential Scanning Calorimetry is about 34° to 37° C.

EXAMPLE 14

Chemically-modified collagen was prepared according to the procedure of Example 12 except that succinic anhydride (0.1 g) was used in place of benzenetricarboxylic anhydride as the amine modifier.

A 2 percent by weight solution of the collagen in BSS TM was colorless and transparent as determined by both visual inspection and light/optical microscopy at 40 x.

The collagen solution (2 percent by weight in a phosphate-buffered solution[13]) is evaluated as an anterior chamber implant in New Zealand white rabbits using the McDonald-Shadduck system in accordance with the procedure described in Example 1. Such evaluation indicates overall equivalence or superiority of the chemically-modified collagen made according to this example with air, BSS TM and Healon TM.

[13] The phosphate-buffered solution contained 0.84 percent by weight NaCl, 0.054 percent by weight KCl, 0.017 percent by weight $CaCl_2$, 0.028 percent by weight $Na_2HPO_4$, and 0.004 percent by weight $NaH_2PO_4$.

The collagen solution (about 2 percent by weight in BSS TM) exhibits the Weissenberg Effect when tested in accordance with the procedure described in Example 1. The collagen solution is pseudoplastic, exhibiting decreasing viscosities at increasing shear rates when tested in accordance with the procedure of Example 1. The collagen solution is thixotropic, recovering about 65 to 95 percent of its initial viscosity within 7 minutes of shearing at 0.1 $sec^{-1}$.

The melt temperature of the 2 percent collagen solution as determined by Differential Scanning Calorimetry is about 34° to 37° C.

EXAMPLE 15

Purified Type I collagen, prepared as in Example 1, is dissolved in enough 0.1M acetic acid to provide a 0.15 percent wt/wt solution. The collagen solution (300 ml) is chilled to 4° C. and the pH is adjusted to 9.0 with 10N NaOH. To the vigorously stirring collagen is added 1,3-benzenedisulfonyl chloride (0.07 g) dissolved in 3 ml ethylene glycol dimethyl ether. The pH is maintained at 9.0±0.25 for 15 minutes by gradual addition of 1 N NaOH.

After 15 minutes, a solution containing 1,2,4-benzenetricarboxylic anhydride (0.05 g) dissolved in 3 ml ethylene glycol dimethyl ether is added to the collagen solution all at once. The pH is maintained at 9.0 ±0.25 for a period of 45 minutes. The pH is increased to 12.0 for 3 minutes by addition of 10 N NaOH. The pH is then reduced to 3.3 using 6 N HCl to precipitate the chemically-modified collagen product. The precipitate is collected by filtration and washed using deionized water. The precipitate is reconstituted in a phosphate-buffered solution[14] to provide a 2 percent wt/wt solution.

[14] The phosphate-buffered solution contained 0.84 percent by weight NaCl, 0.054 percent by weight KCl, 0.017 percent by weight $CaCl_2$, 0.028 percent by weight $Na_2HPO_4$, and 0.004 percent by weight $NaH_2PO_4$.

The collagen solution is colorless and transparent as determined by both visual inspection and light/optical microscopy at 40 x.

The collagen solution is evaluated as an anterior chamber implant in New Zealand white rabbits using the McDonald-Shadduck system in accordance with the procedure described in Example 1. Such evaluation indicates overall equivalence of the chemically-modified collagen made according to this example with air, BSS TM and Healon TM.

The collagen solution (about 2 percent by weight in BSS TM) exhibits the Weissenberg Effect when tested in accordance with the procedure described in Example 1. The collagen solution is pseudoplastic, exhibiting decreasing viscosities at increasing shear rates when tested in accordance with the procedure of Example 1. The collagen solution is thixotropic, recovering about 65 to 95 percent of its initial viscosity within 7 minutes of shearing at 0.1 sec$^{-1}$.

The melt temperature of the 2 percent collagen solution as determined by Differential Scanning Calorimetry is about 34° to 37° C.

EXAMPLE 16

Purified Type I collagen (750 ml), prepared according to Example 3, was treated at 4° C. with 10 N NaOH to raise the pH to 5.0. p-Fluorosulfonylbenzenesulfonyl chloride (0.0251 g) and 0.0124 g glutaric anhydride in 7.5 ml of acetone was added all at once to the vigorously agitating collagen solution. The pH was immediately increased to 11.7 and then decreased to 9.2 by addition of 10 N NaOH and 6 N HCl, respectively. The solution was agitated for 15 minutes to produce the coupled collagen product.

The coupled collagen solution was treated at 4° C. with the dropwise addition of glutaric anhydride (0.0642 g) in 7.5 ml of acetone, and the pH was maintained at 9.0±0.25 by addition of 1 N NaOH. After addition was complete the solution was agitated for 10 minutes. The pH was reduced to 4.0 using 6 N HCl, and the solution was agitated for another 10 minutes. The modified collagen precipitate was collected by centrifugation and washed four times with sterile water at a dilution of 10 parts water to 1 part wet precipitate.

A 2 percent by weight solution of the collagen in BSS TM was colorless and transparent as determined by both visual inspection and light/optical microscopy at 40 x.

The collagen solution 2 percent by weight in BSS TM) was evaluated as an anterior chamber implant in New Zealand white rabbits using the McDonald-Shadduck system in accordance with the procedure described in Example 1. Such evaluation indicated overall equivalence or superiority of the chemically-modified collagen made according to this example with air, BSS TM and Healon TM.

The collagen solution (about 2 percent by weight in BSS TM) exhibits the Weissenberg Effect when tested in accordance with the procedure described in Example 1. The collagen solution is pseudoplastic, exhibiting decreasing viscosities at increasing shear rates when tested in accordance with the procedure of Example 1. The collagen solution is thixotropic, recovering about 65 to 95 percent of its initial viscosity within 7 minutes of shearing at 0.1 sec$^{-1}$.

The melt temperature of the 2 percent collagen solution as determined by Differential Scanning Calorimetry is about 34° to 37° C.

EXAMPLE 17

Purified Type I collagen, as prepared in Example 1, was reconstituted in 300 ml of a 0.1 M acetic acid solution to provide a 0.20 percent wt/wt solution. The collagen solution (300 ml) was chilled to 4° C. and the pH was adjusted to 8.0 with 10 ON NaOH. To the stirring collagen solution was gradually added 5-chlorosulfonyl-o-anisic acid chloride (0.030 g) dissolved in 3 ml acetone, while maintaining the pH at 8.0 by addition of 1 N NaOH. A reaction pH of 8.0 was used in order to reduce the concentration of available free amines thereby controlling the extent of coupling. After 6 minutes of reaction the pH was increased to 13 by addition of 5 N NaOH in order to hydrolyze any remaining coupler and stop the reaction. The pH was maintained at 13 for 2 minutes and then reduced to 9.0 using 6 N HCl.

A solution containing glutaric anhydride (0.034 g) dissolved in 3 ml acetone was added to the collagen solution all at once. The pH was maintained at 9.0±0.25 by gradual addition of 1 N NaOH for a period of 30 minutes. The pH was then reduced to 4.0 using 6 N HCl to precipitate the chemically-modified collagen product. The precipitate was collected and washed according to the method described in Example 1. The collagen precipitate was dissolved in balance salt solution (BSS TM) to provide a 2.0 percent wt/wt solution. The pH was then adjusted to 7.1 using 1 N NaOH.

The collagen solution (2 percent by weight in a phosphate-buffered solution[15]) is evaluated as an anterior chamber implant in New Zealand white rabbits using the McDonald-Shadduck system in accordance with the procedure described in Example 1. Such evaluation indicates overall equivalence of the chemically-modified collagen made according to this example with air, BSS TM and Healon TM.

[15] The phosphate-buffered solution contained 0.84 percent by weight NaCl, 0.054 percent by weight KCl, 0.017 percent by weight CaCl$_2$, 0.028 percent by weight Na$_2$HPO$_4$, and 0.004 percent by weight NaH$_2$PO$_4$.

The collagen solution (about 2 percent by weight in BSS TM) exhibits the Weissenberg Effect when tested in accordance with the procedure described in Example 1. The collagen solution is pseudoplastic, exhibiting decreasing viscosities at increasing shear rates when tested in accordance with the procedure of Example 1. The collagen solution is thixotropic, recovering about 65 to 95 percent of its initial viscosity within 7 minutes of shearing at 0.1 sec$^{-1}$.

The melt temperature of the 2 percent collagen solution as determined by Differential Scanning Calorimetry is about 34° to 37° C.

What is claimed is:

1. A chemically-modified collagen compound which comprises at least two native collagen molecules which are coupled at at least one lysine epsilon amino group present on each said collagen molecule by a coupling group, said coupling group comprising at least two moieties selected from the group consisting of carbonyl and sulfonyl groups.

2. The chemically-modified collagen compound of claim 1 wherein said carbonyl and/or sulfonyl groups present in said coupling group are linked to each other through saturated or unsaturated alkylene, arylene or mixed alkylene-arylene coupling chains having less than about twenty carbon atoms, wherein said alkylene and/or arylene coupling chains may also contain heteroatoms selected from the group consisting of oxygen, sulfur and nitrogen, and may be substituted in available aromatic positions by carboxyl groups, straight or branched chain alkyl groups of about 1 to 4 carbon atoms, straight or branched chain alkoxy groups of about 1 to 4 carbon atoms, halogens and other non-reactive moieties, and in available aliphatic positions by carboxyl groups and alkyl or alkoxy groups of about 1 to 4 carbon atoms.

3. The chemically-modified collagen compound of claim 1 wherein said coupling group has the general formula:

—B—A—B— wherein

B is independently CO, SO₂ or combinations thereof; and

A is selected from the group consisting of:
(1) an aromatic group having about 6 to 20 carbon atoms;

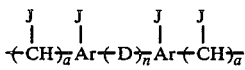

wherein

Ar is independently selected from the group consisting of an aromatic ring having 6 to 10 carbon atoms, a heteroaromatic ring containing atoms selected from the group consisting of C, N, O and S, and having about 5 to 10 atoms, or combinations thereof;

J is hydrogen or $-(L)_b-B$, wherein L is selected from the group consisting of phenylene, an alkylene of about 1 to 4 carbon atoms, and an oxyalkylene of about 1 to 4 carbon atoms, b is 0 or 1, and B is as defined hereinabove, with the proviso that only one J in the chain

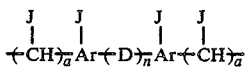

may be $-(L)_b-B$, with all other J's being hydrogen;

n is 0 or 1;

a is 0 or an integer having a value of between about 1 and 4; and

D is independently selected from the group consisting of O, CO, S, SO, SO₂,

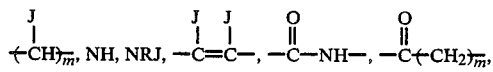

—SO₂—NH—, —NH—CO—NH—, wherein m is an integer having a value of between about 1 and 3, R is selected from the group consisting of phenyl, and a straight or branched chain alkyl or acyl group having 1 to 4 carbon atoms; and J is as defined and restricted hereinabove;

(3) an aromatic group having about 6 to 10 carbon atoms, wherein said aromatic group may be substituted in available positions by J wherein J is as defined and restricted hereinabove;

(4) a heteroaromatic group containing atoms selected from the group consisting of C, N, O and S, and having from about 5 to 14 ring atoms, wherein said heteroaromatic group may be substituted in available positions by J, wherein J is as defined and restricted hereinabove;

(5) an aliphatic or arylaliphatic chain which contains one or two olefinic or acetylenic groups and which contains about 2 to 20 carbon atoms, wherein said chain may be substituted in available positions by J, wherein J is as defined and restricted hereinabove;

(6) an alicyclic ring which may be partially unsaturated, having about 3 to 15 carbon atoms, wherein said alicyclic ring may be substituted in available positions by J wherein J is as defined and restricted hereinabove;

(7) a heterocyclic ring which may be saturated or unsaturated and which contains atoms selected from the group consisting of C, N, O and S, which has from about 5 to 12 ring atoms, wherein said heterocyclic ring may be substituted in available positions by J wherein J is as defined and restricted hereinabove;

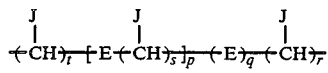

wherein t is an integer having a value of between about 1 and 8;

E is independently selected from the group consisting of O, NRJ, S, SO, SO₂, CO,

CONH, SO₂NH and NHCONH, wherein R is as defined hereinabove, and m is an integer having a value of between about 1 and 3;

J is as defined and restricted hereinabove;

s is an integer having a value of between about 2 and 8;

p is 0 or an integer having a value of between about 1 and 4;

q is about 0 or 1; and r is 0 or an integer having a value of between about 1 and 8, provided that when q is 1, r is greater than 0; and

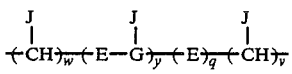

wherein

G is independently selected from the group consisting of an aromatic ring having about 6 to 10 carbon atoms, a heteroaromatic ring having about 5 to 10 atoms, and a heterocyclic ring having about 5 to 10 atoms, wherein the heteroaromatic and heterocyclic rings contain atoms selected from the group consisting of C, N, O and S;

J is as defined and restricted hereinabove;

w is an integer having a value of between about 1 and 8;

E and q are as defined hereinabove;

y is about 1 or 2; and v is 0 or an integer having a value of between about 1 and 4, provided that when q is 1, v is not 0.

4. The chemically-modified collagen compound of claim 3 wherein A is selected from the group consisting of:

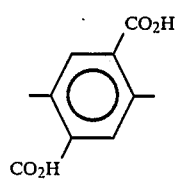

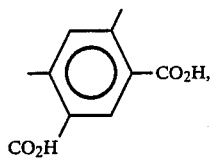

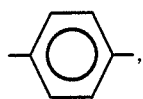

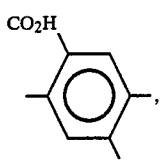

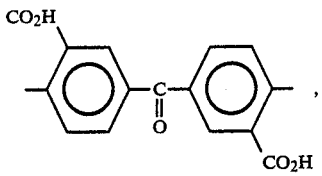

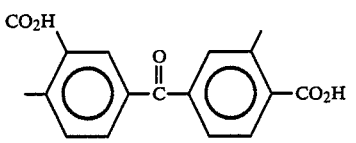

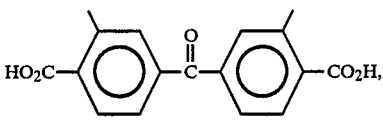

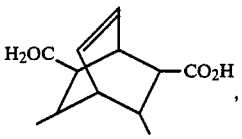

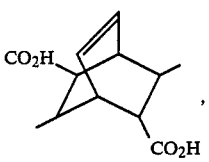

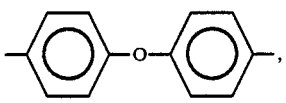

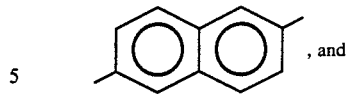, and

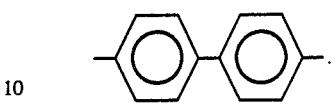.

5. The chemically-modified collagen compound of claim 3 wherein B is CO and A is $-(CH_2)_2-$.

6. The chemically-modified collagen compound of claim 1 wherein at least a portion of the lysine epsilon amino groups which are not linked to said coupling groups are linked to amine-modifying groups, which amine-modifying groups are selected from the group consisting of saturated or unsaturated alkane sulfonamide and carboxamide groups, arene sulfonamide and carboxamide groups and mixed saturated or unsaturated alkane-arene sulfonamide and carboxamide groups, which amine-modifying groups have between about 2 and 20 carbon atoms and are terminated by one or two carboxylic or sulfonic acid moieties, wherein said amine-modifying group may also contain up to 5 heteroatoms selected from the group consisting of oxygen, sulfur and nitrogen, and may be substituted in available aromatic and aliphatic positions by carboxyl groups, alkyl and alkoxy groups having about 1 to 4 carbon atoms and halogens.

7. The chemically-modified collagen compound of claim 1 wherein at least about 60 percent of the lysine epsilon amino groups which are not linked to said coupling groups are linked to amine-modifying groups, which amine-modifying groups are selected from the group consisting of saturated or unsaturated alkane sulfonamide and carboxamide groups, arene sulfonamide and carboxamide groups and mixed saturated or unsaturated alkane-arene sulfonamide and carboxamide groups, which amine-modifying groups have between about 2 and 20 carbon atoms and are terminated by one or two carboxylic or sulfonic acid moieties, wherein said amine-modifying group may also contain up to 5 heteroatoms selected from the group consisting of oxygen, sulfur and nitrogen, and may be substituted in available aromatic and aliphatic positions by carboxyl groups, alkyl and alkoxy groups having about 1 to 4 carbon atoms and halogens.

8. A collagen fraction comprised of collagen molecules, about 10 to 80 percent of which comprise the chemically-modified collagen compound of claim 1, with all of the remaining collagen molecules being uncoupled.

9. A collagen fraction comprised of collagen molecules, about 10 to 80 percent of which comprise the chemically-modified collagen compound of claim 7.

10. A viscoelastic collagen solution comprising about 0.5 to 5.0 percent by weight of the collagen fraction of claim 9 dissolved in a physiological buffer solution.

11. A viscoelastic collagen solution comprising about 0.5 to 5.0 percent by weight of the collagen compound of claim 6 dissolved in a physiological buffer solution, wherein the coupling group is present in said chemically-modified collagen compound to such an extent that a 2 percent by weight solution of said collagen compound in said physiological buffer has a steady state viscosity of about 0.15 to $10^6$ to about $4.0 \times 10^6$ centipoise at a shear rate of about 0.10 seconds$^{-1}$; a steady state viscosity of about $0.20 \times 10^5$ to about $7.5 \times 10^5$ centipoise at a shear rate of about 1.0 seconds$^{-1}$; a steady state viscosity of about $0.3 \times 10^4$ to about $1.0 \times 10^5$ centipoise at a shear rate of about 10.0 seconds$^{-1}$; and a steady state viscosity of about $0.45 \times 10^3$ to about $2.0 \times 10^4$ centipoise at a shear rate of about 100 seconds$^{-1}$.

12. A viscoelastic collagen solution comprising about 0.5 to 5.0 percent by weight of the collagen compound of claim 6 dissolved in a physiological buffer solution, wherein the coupling group is present in said chemically-modified collagen compound to such an extent that a 2 percent by weight solution of said collagen compound in said physiological buffer has a melt temperature of between about 32° C. and 48° C.

13. The viscoelastic collagen solution of claim 11 wherein said coupling group is —CO-(-CH$_2$)$_2$—CO—, and said modifying group is —CO-(-CH$_2$-)-$_2$CO$_2$H.

14. The viscoelastic collagen solution of claim 11 wherein said coupling group is —CO-(-CH$_2$)$_3$—CO$_2$H. modifying group is —CO(CH$_2$)$_3$—CO$_2$H.

15. A method of making a chemically-modified collagen compound comprising the steps of
  (a) adding to an aqueous solution of at least about 0.05 percent by weight native collagen, a coupling agent in an amount equal to about 1 to 600 moles of coupling agent per mole of native collagen, said coupling agent selected from the group consisting of di- and tri-carboxylic acid halides, di- and tri-sulfonyl halides, di- and tri-anhydrides, di- and tri-reactive active esters, and compounds having at least two moieties selected from the group consisting of carboxylic acid halide, sulfonyl halide, anhydride and active ester; and
  (b) reacting said native collagen and said coupling agent at a pH of above about 8 and at a temperature of between about 0° and 35° C., for a time period sufficient to either react or hydrolyze substantially all of said coupling agent.

16. The method of claim 15 wherein said coupling agent is selected from the group consisting of terephthaloyl chloride; bicyclo-(2,2,2)-oct-7-ene-2,3,5,6-tetracarboxylic-2,3,5,6-dianhydride; 1,2,4,5-benzenetetracarboxylic dianhydride; p-fluorosulfonylbenzenesulfonyl chloride; and wherein the pH of the reaction mixture is initially maintained at about 3 to about 5.5 before raising the pH to above about 8.

17. The method of claim 15 wherein said method additionally comprises the steps of:
  (c) adding to said reaction mixture a mono-reactive amine-modifying agent, said amine-modifying agent being selected from the group consisting of anhydrides, acid halides, sulfonyl halides and active esters, in an amount equal to at least about 100 moles of amine-modifying agent per mole of native collagen; and
  (d) conducting the amine-modification reaction at a pH of greater than about 8 and at a temperature of between about 0° and 35° C., for a time period sufficient to either react or hydrolyze substantially all of said amine-modifying agent.

18. A method of making a chemically-modified collagen compound comprising the steps of:
  (a) adding to an aqueous solution of at least about 0.05 percent by weight native collagen, a coupling agent in an amount equal to about 1 to 600 moles of coupling agent per mole of native collagen and a mono-reactive amine-modifying agent in an amount equal to at least about 50 moles of amine-modifying agent per mole of native collagen; said coupling agent selected from the group consisting of di- and tri-carboxylic acid halides, di- and tri-sulfonyl halides, di- and tri-anhydrides, di- and tri-reactive active esters and compounds having at least two moieties selected from the group consisting of carboxylic acid halide, sulfonyl halide, anhydride and active ester; and wherein said amine-modifying agent is selected from the group consisting of anhydrides, acid halides, sulfonyl halides and active esters;
  (b) allowing the reaction mixture to react at a pH of greater than about 8 and at a temperature of between about 0° and 35° C., for a time period sufficient to either react or hydrolyze substantially all of said coupling agent and said amine-modifying agent;
  (c) adding to the reaction mixture of step (b) additional mono-reactive amine-modifying agent in an amount equal to at least about 50 moles of modifying agent per mole of native collagen; and
  (d) allowing the reaction mixture of step (c) to react at a pH of greater than about 8 and at a temperature of between about 0° and 35° C., for a period of time sufficient to either react or hydrolyze substantially all of said modifying agent.

19. A method of making a chemically-modified collagen compound comprising the steps of:
  (a) adding to an aqueous solution of at least about 0.05 percent by weight native collagen a mono-reactive amine-modifying agent in an amount equal to at least about 25 moles of amine-modifying agent per mole of native collagen, said amine-modifying agent being selected from the group consisting of anhydrides, acid halides, sulfonyl halides and active esters;
  (b) allowing the reaction mixture of step (a) to react at a pH of greater than about 8 and at a temperature of about 0° to 35° C. for a period of time sufficient to either react or hydrolyze substantially all of said amine-modifying agent;
  (c) adding to the mixture produced in step (b) a coupling agent in an amount equal to about 1 to 600 moles of coupling agent per mole of native collagen; said coupling agent selected from the group consisting of di- and tri-carboxylic acid halides, di- and tri-sulfonyl halides, di- and tri-anhydrides and di- and tri-reactive active esters, and compounds having at least two moieties selected from the group consisting of carboxylic acid halide, sulfonyl halide, anhydride and active ester; and
  (d) allowing the reaction mixture of step (c) to react at a pH of greater than about 8 and at a temperature of about 0° to 35° C. for a time period sufficient to either react or hydrolyze substantially all of said coupling agent;
  (e) adding to the reaction mixture of step (d) additional amine-modifying agent in a concentration of at least about 75 moles of modifying agent per mole of native collagen; and
  (f) allowing the reaction mixture of step (d) to react at a pH of greater than about 8, and at a temperature of between about 0° and 35° C., for a period of time sufficient to either react or hydrolyze substantially all of said amine-modifying agent.

20. A method of replacing at least a portion of the aqueous or vitreous humor in a human or animal eye, said method comprising introducing into the aqueous or vitreous chamber of said human or animal eye, an effective amount of the viscoelastic collagen solution of claim 12.

21. A method of inserting an intraocular lens into the anterior or posterior chamber of a human or animal eye, said method comprising introducing into said anterior or posterior chamber an amount of the viscoelastic solution of claim 12 sufficient to reduce the trauma which normally results from inserting an intraocular lens into said chamber without the use of a viscoelastic ophthalmic aid.

22. A method of preventing fibrous tissue formation and consequent development of adhesion and scars which may occur in healing tissue during the normal healing process, said method comprising introducing into a surgical site, either during surgery or post-operatively an effective amount of the viscoelastic solution of claim 12.

23. A method of reducing inflammation and promoting the normal healing of soft tissues and cartilage, said method comprising introducing by injection into the affected soft tissue or cartilage an effective amount of the viscoelastic solution of claim 12.

24. A method of enhancing normal joint and tendon function in a human or animal by lubricating said joint or tendon, said method comprising introducing into the synovial space associated with said joint or tendon an effective lubricating amount of the viscoelastic solution of claim 12.

25. A method of separating healing tissues and maintaining said separation during the normal healing process after surgery, said method comprising introducing into a surgical site, either during surgery or post-operatively, an effective amount of the viscoelastic solution of claim 12.

26. A method of protecting a layer of tissue during surgery on an adjacent layer of tissue, said method comprising introducing into the surgical site an amount of the viscoelastic solution of claim 12 effective to prevent dislocation and movement of said tissue.

27. A method of protecting soft tissue and cartilage from the possible harmful effects of prosthetic implants, said method comprising coating said implant with an effective lubricating amount of the viscoelastic solution of claim 12.

28. A method of achieving hemostasis comprising placing an effective amount of the chemically-modified collagen compound of claim 1 in contact with a bleeding wound.

29. A method of achieving hemostasis comprising placing an effective amount of the chemically-modified collagen compound of claim 7 in contact with a bleeding wound.

30. A method of augmenting soft tissue comprising placing an effective amount of the chemically-modified collagen compound of claim 1 in contact with the augmentation site.

31. A method of augmenting soft tissue comprising placing an effective amount of the chemically-modified collagen compound of claim 7 in contact with the augmentation site.

* * * * *

UNITED STATES PATENT AND TRADEMARK OFFICE
CERTIFICATE OF CORRECTION

PATENT NO. : 4,713,446

DATED : December 15, 1987

INVENTOR(S) : Dale P. Devore, Robert A. Scherrer and Matthew T. Scholz

It is certified that error appears in the above-identified patent and that said Letters Patent is hereby corrected as shown below:

Column 1, Line 7 "and now abandoned" should be deleted.
Column 4, Line 43 --(8)-- should be added before the formula; and in Line 64 --(9)-- should be added before the formula.
Column 11, lines 19 and 20, "substantially all of" should be deleted; and in line 21, before "any", --substantially all of-- should be added.
Column 19, lines 39, 41 and 44 "sec" should be --$sec^{-1}$--.
Column 29, line 59 "10 ON NaOH" should be --10 N NaOH--.

Signed and Sealed this

Eighth Day of August, 1989

Attest:

DONALD J. QUIGG

Attesting Officer

Commissioner of Patents and Trademarks